US008092380B2

(12) United States Patent
Rothman et al.

(10) Patent No.: US 8,092,380 B2
(45) Date of Patent: Jan. 10, 2012

(54) SYSTEM AND METHOD FOR IMPROVING HOSPITAL PATIENT CARE BY PROVIDING A CONTINUAL MEASUREMENT OF HEALTH

(75) Inventors: Michael Rothman, Hopewell Junction, NY (US); Steven Rothman, Monticello, NY (US)

(73) Assignee: Rothman Healthcare Corporation, Sarasota, FL (US)

( * ) Notice: Subject to any disclaimer, the term of this patent is extended or adjusted under 35 U.S.C. 154(b) by 1131 days.

(21) Appl. No.: 11/362,450

(22) Filed: Feb. 24, 2006

(65) Prior Publication Data

US 2006/0206013 A1    Sep. 14, 2006

Related U.S. Application Data

(60) Provisional application No. 60/657,365, filed on Feb. 28, 2005.

(51) Int. Cl.
*A61B 5/00* (2006.01)
*G06Q 10/00* (2006.01)
*G06Q 50/00* (2006.01)

(52) U.S. Cl. ................. 600/300; 600/301; 705/2; 705/3
(58) Field of Classification Search ........................ None
See application file for complete search history.

(56) References Cited

U.S. PATENT DOCUMENTS

| 5,074,980 | A | 12/1991 | Vasta-Russell et al. ...... 204/182 |
| 5,850,339 | A | 12/1998 | Giles |
| 6,193,654 | B1 | 2/2001 | Richardson et al. .......... 600/300 |
| 6,336,903 | B1 * | 1/2002 | Bardy ........................... 600/508 |
| 6,438,419 | B1 * | 8/2002 | Callaway et al. ................. 607/5 |
| 6,790,178 | B1 * | 9/2004 | Mault et al. ................... 600/300 |
| 6,960,167 | B2 | 11/2005 | Bardy |
| 7,003,341 | B2 | 2/2006 | Say et al. ...................... 600/345 |
| 7,031,857 | B2 | 4/2006 | Tarassenko et al. ............ 702/67 |
| 7,081,091 | B2 | 7/2006 | Merrett et al. |
| 7,213,009 | B2 | 5/2007 | Pestotnik et al. .............. 706/46 |
| 7,454,359 | B2 | 11/2008 | Rosenfeld et al. |

(Continued)

FOREIGN PATENT DOCUMENTS

GB    2 392 750    10/2004

(Continued)

OTHER PUBLICATIONS

Abraham, Edward, "Glucose-6-Phosphate Dehydrogenase and Sepsis: The Jury is Still Out", Crit Care Med., Editorial, vol. 35, No. 2 (2007) pp. 655-656.

(Continued)

*Primary Examiner* — Sam Yao
*Assistant Examiner* — Shirley Jian
(74) *Attorney, Agent, or Firm* — Greenberg Traurig, LLP; David J. Dykeman; Danielle T. Abramson

(57) ABSTRACT

A system for improving hospital patient care by generating a Health Score. The system includes an interface module for receiving incoming medical data from a patient, a transformation module for transforming each of the medical datum into a transformed Health Score value, and a combination module for combining the transformed Health Score values corresponding to each of the medical datum into a single Health Score. A presentation and comparison module displays the Health Score as a Health Score plot over a predetermined time frame, such that a user may identify health trends in a patient by evaluating said Health Score plot.

20 Claims, 12 Drawing Sheets

U.S. PATENT DOCUMENTS

| | | | |
|---|---|---|---|
| 2002/0026104 A1 | 2/2002 | Bardy | 600/300 |
| 2003/0208106 A1* | 11/2003 | Anderson et al. | 600/300 |
| 2003/0225315 A1* | 12/2003 | Merrett et al. | 600/300 |
| 2005/0187796 A1 | 8/2005 | Rosenfeld et al. | 705/3 |
| 2006/0161459 A9 | 7/2006 | Rosenfeld et al. | 705/3 |
| 2006/0200009 A1 | 9/2006 | Wekell et al. | |
| 2006/0206012 A1 | 9/2006 | Merrett et al. | |
| 2006/0287906 A1 | 12/2006 | McGillin | 705/9 |
| 2009/0105550 A1 | 4/2009 | Rothman et al. | 600/300 |
| 2010/0100392 A1 | 4/2010 | Rothman et al. | |

FOREIGN PATENT DOCUMENTS

| | | |
|---|---|---|
| WO | WO 02/21313 | 3/2002 |
| WO | WO 03/082097 | 10/2003 |
| WO | WO 2006/093807 | 9/2006 |
| WO | WO 2008/045577 | 4/2008 |
| WO | WO 2010/048282 | 4/2010 |

OTHER PUBLICATIONS

Aiken et al., "Hospital Nurse Staffing and Patient Mortality, Nurse Burnout, and Job Dissatisfaction", JAMA, vol. 288, No. 16 (Oct. 23-30, 2002) pp. 1987-1993.

Alam, Hasan B., "To Cool or Not to Cool, That is the Question", Crit Care Med., Editorial, vol. 35, No. 2 (2007) pp. 660-662.

Aneman et al., "The ERC Guidelines for Resuscitation 2005 and the Medical Emergency Team", Scand J Trauma Resusc Emerg Med, vol. 14 (2006), pp. 74-77.

Asai, Takashi, "How Should We Use Prokinetic Drugs in Patients who are Intolerant to Enteral Feeding?", Crit Care Med., Editorial, vol. 35, No. 2 (2007) pp. 650-651.

Baggs, Judith G., "Nurse-Physician Collaboration in Intensive Care Units", Crit Care Med., Editorial, vol. 35, No. 2 (2007) pp. 641-642.

Baggs, Judith G., "Prognostic Information Provided During Family Meetings in the Intensive Care Unit", Crit Care Med., Editorial, vol. 35, No. 2 (2007) pp. 646-647.

Bates et al., "Improving Safety with Information Technology", N Engl J Med, vol. 348, No. 25 (Jun. 19, 2003) pp. 2526-2534.

Bensen et al., "To be or Not to be (in the Intensive Care Unit)-Is that a Question?", Crit Care Med., Editorial, vol. 35, No. 2 (2007) pp. 647-648.

Berman et al., "Validation of the 2000 Bernstein-Parsonnet Score Versus the EuroSCORE as a Prognostic Tool in Cardiac Surgery", Ann Thorac Surg, vol. 86 (2006) pp. 537-541.

Berms, John J., "Ischemia-Reperfusion: Putting the Pieces of the Puzzle Together", Crit Care Med., Editorial, vol. 34, No. 5 (2006) pp. 1570-1571.

Bion et al., "Improving the Reliability of Healthcare Systems' Responsiveness to the Needs of Acutely Ill Patients", Crit Care Med., Editorial, vol. 35, No. 2 (2007) pp. 637-639.

Braden et al., "Braden Scale for Predicting Pressure Sore Risk" (1988).

Brander et al.. "Exophageal and Transpulmonary Pressure Help Optimize Mechanical Ventilation in Patients with Acute Lung Injury", Crit Care Med., Editorial, vol. 34, No. 5 (2006) pp. 1556-1558.

Brennan et al., "Accidental Deaths, Saved Lives, and Improved Quality", N Engl J Med, vol. 353, No. 13 (Sep. 29, 2005) pp. 1405-1409.

Clark et al., "Concurrent Prediction of Hospital Mortality and Length of Stay From Risk Factors on Admission", vol. 37, No. 3 (Jun. 2002) pp. 631-645.

Clinton et al., "Making Patient Safety the Centerpiece of Medical Liability Reform", N Engl J Med, vol. 354, No. 21 (May 25, 2006), pp. 2205-2208.

Cole, Randolph P., "Predicting Response to Fluid Administration: Something Old, Something New?", Crit Care Med., Editorial, vol. 34, No. 5 (2006) pp. 1559-1560.

Coimbra, Raul, "Salt in the Vein, Good for the Brain . . . ", Crit Care Med., Editorial, vol. 35, No. 2 (2007) pp. 659-660.

Cretikos et al., "The Objective Medical Emergency Team Activation Criteria: A Case-Control Study", Resuscitation, Vo.. 73 (2007) pp. 62-72.

Crippen, David, "Comfortably Numb in the Intensive Care Unit", Crit Care Med., Editorial, vol. 34, No. 5 (2006) pp. 1558-1559.

Cuthbertson, B.H., "Can Physiological Variables and Early Warning Scoring Systems Allow Early Recognition of the Deteriorating Surgical Patient?", Crit Care Med, vol. 35, No. 2 (2007) pp. 402-409.

Cuthbertson, B.H., "Editorial II: Outreach Critical Care-Cash for No Questions", British Journal of Anesthesia, Editorial II (2003) pp. 4-6.

DeVita et al., "Findings of the First Consensus Conference on Medical Emergency Teams", Crit Care Med, vol. 34, No. 9 (2006) pp. 2463-2478.

Dupuydt et al., "Antiobiotic Therapy for Ventilator-Associated Pneumonia: De-Escalation in the Real World", Crit Care Med., Editorial, vol. 35, No. 2 (2007) pp. 632-633.

Engle, Toby R. MD "Electrocardiographic Diagnosis of Coronary Syndromes in the Critical Care Unit", Crit Care Med., Editorial, vol. 34, No. 5 (2006) pp. 1546-1547.

Epstein, Scott K, MD "Preventing Prostextubation Respiratory Failure", Crit Care Med., Editorial, vol. 34, No. 5 (2006) pp. 1547-1548.

Erikkson, Urs, "Chlamydia and Myocarditis: An Old Bug Bugging Seriously", Crit Care Med., Editorial, vol. 35, No. 2 (2007) pp. 665.

Finster et al., "The Apgar Score has Survived the Test of Time", Anesthesiology, Vo. 102, No. 4 (Apr. 2005) pp. 855-857.

Forster et al., "Adverse Events Among Medical Patients After Discharge", CMAJ, vol. 170, No. 3 (Feb. 3, 2004) pp. 345-349.

Fraser et al., "Comfort without Coma: Changing Sedation Practices", Crit Care Med., Editorial, vol. 35, No. 2 (2007) pp. 635-637.

Friedman et al., "The Rate and Cost of Hospital Readmissions for Preventable Conditions", MCR&R, vol. 61, No. 2 (Jun. 2004), pp. 225-240.

Gao et al., "Systematic Review and Evaluation of Physiological Track and Trigger Warning Systems for Identifying At-Risk Patients on the Ward", Intensive Care Med, vol. 33 (2007) pp. 667-679.

Gentilello, Larry M., "Alcohol and the Intensive Care Unit: It's Not Just an Antiseptic", Crit Care Med., Editorial, vol. 35, No. 2 (2007) pp. 627-628.

Gogbashian et al., "EuroSCORE: A Systematic Review of International Performance", European Journal of Cario-thoracic Surgery, vol. 25 (2004) pp. 695-700.

Goldhill, David R., "Editorial: of Missiles and Medicine: Early Warning Systems", Anesthesia, vol. 61 (2006) pp. 209-214.

Goldhill et al., "Physiological Values and Procedures in the 24 h Before ICU Admission from the Ward", Anesthesia, vol. 54 (1999) pp. 529-534.

Goldstein, Brahm, "How Do We Get From Here to There? a Pathway for Trial Design in Complex Systems Analysis", Crit Care Med., Editorial, vol. 35, No. 2 (2007) pp. 656-658.

Goodacre et al., "Prediction of Mortality Among Emergency Medical Admissions", Emerg Med J, vol. 23 (2006), pp. 372-375.

Greenhalgh, David G., "Hypoxic Pulmonary Vasoconstriction After Combined Burn and Inhalation Injury", Crit Care Med., Editorial, vol. 34, No. 5 (2006) pp. 1562-1563.

Groeneveld et al. "Catecholamines, Parasympathetic Stimuli, or Cortisol for Overwhelming Sepsis", Crit Care Med., Editorial, vol. 34, No. 5 (2006) pp. 1549-1550.

Hager, et al. "Customizing Lung-Protective Mechanical Ventilation Strategies", Crit Care Med., Editorial, vol. 34, No. 5 (2006) pp. 1554-1555.

Hart, G.K., "Editorial: Antecedents to Hospital Deaths: All in Good Time", Internal Medical Journal, vol. 31 (2001) pp. 321.

Herlitz et al., "Characteristics and Outcome Among Patients Suffering In-Hospital Cardiac Arrest in Monitored and Non-Monitored Areas", Resuscitation, vol. 48 (2001) pp. 125-135.

Herlitz et al., "Very High Survival Among Patients Defibrillated at an Early Stage After In-Hospital Ventricular Fibrillation on Wards With and Without Monitoring Facilities", Resuscitation, vol. 66 (2005) pp. 159-166.

Hillman et al., "Antecedents to Hospital Deaths", Internal Medical Journal, vol. 31 (2001) pp. 343-348.

Hillman et al., "Introduction of the Medical Emergency Team (MET) System: a Cluster-Randomised Controlled Trial", Lancet, vol. 365 (Jun. 18, 2005), pp. 2091-2097.

Hovda et al., "Oxidative Need and Oxidative Capacity Following Traumatic Brain Injury", Crit Care Med., Editorial, vol. 35, No. 2 (2007) pp. 663-664.

Hravnak, Marilyn, "Electronic Integrated Monitoring of Medical Emergency Team Calls to a Step Down Unit", This is Biosigns Presentation, (Jun. 2006).

Jacobs, et al., "Increasing Vigilance on the Medical/Surgical Floor to Improve Patient Safety", Journal of Advanced Nursing, vol. 57, No. 5 (2007) pp. 472-781.

Kause et al., "A Comparison of Antecedents to Cardiac Arrests, Deaths and Emergency Intensive Care Admissions in Australia and New Zealand, and the United Kingdom-the Academia Study", Resuscitation, vol. 62 (2004) pp. 275-282.

Knaus et al., "The Apache III Prognostic System. Risk Prediction of Hospital Mortality for Critically Ill Hospitalized Adults", Chest, vol. 100 (1991) pp. 1619-1636.

Kramer et al. "Uniform Patient Assessment for Post-Acute Care", Division of Health Care Policy and Research, UCDHSC, Aurora, CO (Jan. 25, 2006), pp. 1-135.

Knoefel, Wolfram Trudo, "The Peritonitis Dilemma: Better Safe Than Sorry or Wait for the Cat to Jump", Crit Care Med., Editorial, vol. 35, No. 2 (2007) pp. 648-649.

Kruger et al., "Nonuse of Statins-A New Risk Factor for Infectious Death in Cardiovascular Patients", Crit Care Med., Editorial, vol. 35, No. 2 (2007) pp. 631-632.

Krumholz et al., "Randomized Trial of an Education and Support Intervention to Prevent Readmission of Patients with Heart Failure", JACC, vol. 39, No. 1 (Jan. 2, 2002) pp. 83-89.

Kucher et al., "Electronic Alerts to Prevent Venous Thromboembolism Among Hospitalized Patients", vol. 352, No. 10 (Mar. 10, 2005) pp. 969-977.

Landesberg et al., "Silent Myocardial Ischemia in the Noncoronary Intensive Care Unit: A New Frontier?", Crit Care Med., Editorial, vol. 35, No. 2 (2007) pp. 629-630.

Lemaire, Francois, "Low-Dose Perfluorocarbon: A Revival for Partial Liquid Ventilation", Crit Care Med., Editorial, vol. 35, No. 2 (2007) pp. 662-663.

Leonhardt, David, "Why Doctors So Often Get it Wrong", New York Times, (Feb. 22, 2006), available at http://www.nytimes.com/2006/02/22/business/22leonhardt.html?_r=1&pagewanted=print &oref=slogin (last visited Jan. 14, 2008).

Lohr et al., "Smart Care Via a Mouse, but What Will it Cost?", New York Times, (Aug. 20, 2006), available at http://www.nytimes.com/2006/08/20/business/yourmoney/20info.html?_r=1 &pagewanted=print&oref=slogin (last visited Jan. 14, 2008).

Luce, John. M., "Acknowledging our Mistakes", Crit Care Med., Editorial, vol. 34, No. 5 (2006) pp. 1575-1576.

Luna, Carlos M., "Modulating the Oral Colonization with Povidone-iodine Antiseptic: A New Approach for an Old Controversy", Crit Care Med., Editorial, vol. 34, No. 5 (2006) pp. 1572-1573.

Machado, Roberto F., "Nitric-Oxide Based Therapies in Sickle Cell Disease: The Evidence Continues to Mount", Crit Care Med., Editorial, vol. 35, No. 2 (2007) pp. 654-655.

Marini, John, J.. Lessons Learned: The Conditional Importance of High Positive End-Expiratory Pressure in Acute Respiratory Distress Syndrome, Crit Care Med., Editorial, vol. 34, No. 5 (2006) pp. 1540-1542.

Mimoz et al., "Prevention of Ventilator-Associated Pneumonia: Do Not Forget to Disinfect the Mouth", Crit Care Med., Editorial, vol. 35, No. 2 (2007) pp. 668-669.

Morgan et al., "An Early Warning Scoring System for Detecting Developing Critical Illness", Clinical Intensive Care, vol. 8, No. 2 (1997), pp. 11.

Morris, Alan H., MD "Extracorporeal Support and Patient Outcome: Credible Causality Remains Elusive", Crit Care Med., Editorial, vol. 34, No. 5 (2006) pp. 1551-1552.

Mundow, Anna, "A Cut Above?", Irish Times, (May 26, 2007).

Muhl, Heiko, "Controlling the Cytokine Storm y Insulin: Glycogen Synthase Kinase-3 as a Target in Systemic Inflammation", Crit Care Med., Editorial, vol. 34, No. 5 (2006) pp. 1567-1569.

Nasraway Stanley A., Jr., "'Search and Destroy' for Methicillin-Resistant *Staphylococcus aureus* in the Intensive Care Unit: Should This Now be the Standard of Care?", Crit Care Med., Editorial, vol. 35, No. 2 (2007) pp. 642-644.

Needham et al., "Critically Appraise Before you Believe: The Quality of Meta-Analyses in Critical Care Medicine", Crit Care Med., Editorial, vol. 35, No. 2 (2007) pp. 666-667.

Nozari, Ala, "Tuning Up the Compression and Applying the Choke for Better Horsepower in Resuscitation", Crit Care Med., Editorial, vol. 34, No. 5 (2006) pp. 1563-1564.

O'Rourke, Michael F., "Pressure Pulse Waveform Analysis in Critical Care", Crit Care Med., Editorial, vol. 34, No. 5 (2006) pp. 1569-1570.

Papadakos, Peter J., Md "The Long and Short of Sedation Practices: Daily Interruption or Bolus Sosing?", Crit Care Med., Editorial, vol. 34, No. 5 (2006) pp. 1544-1545.

Parienti et al., "Viral Pneumonia and Respiratory Sepsis: Association, Causation, or it Depends", Crit Care Med., Editorial, vol. 35, No. 2 (2007) pp. 639-640.

Parissopoulos et al., "Critical Care Outreach and the Use of Early Warning Scoring Systems; A Literature Review", Icus Nurs Web J, Issue 21, (Jan.-Mar. 2005), pp. 1-13.

Pear, Robert, "A.M.A. To Develop Measurement of Quality of Medical Care", New York Times, (Feb. 21, 2006), available at http://www.nytimes.com/2006/02/21/politics/21docs.html?pagewanted=print (last visited Jan. 14, 2008).

Plost et al., "Family Care in the Intensive Care Unit: The Golden Rule, Evidence, and Resources", Crit Care Med., Editorial, vol. 35, No. 2 (2007) pp. 669-670.

Rand Corporation, "An Argument for Electronic Records", New York Times, (Aug. 19, 2006).

Reilly et al., "Translating Clinical Research into Clinical Practice: Impact of Using Prediction Rules to Make Decisions", Ann Intern Med, vol. 144 (2006) pp. 201-209.

Rexius et al., "A Simple Score to Assess Mortality Risk in Patients Waiting for Coronary Artery Bypass Grafting", Ann Thorac Surg, vol. 81 (2006) pp. 577-582.

Sarasota's Guidelines for When to Call a Rapid Response Team (as seen by BJR posted on East Tower, floor 9), (Apr. 18, 2007).

Sheridan, Rob, "Reducing Blood Loss in Burn Care", Crit Care Med., Editorial, vol. 35, No. 2 (2007) pp. 665.

Sirio, Carl A. "Critical Care Performance Measurement: The Time has Come for All", Crit Care Med., Editorial, vol. 34, No. 5 (2006) pp. 1538-1539.

Southern et al., "Hospitals Care and Length of Stay in Patients Requiring Complex Discharge Planning and Close Clinical Monitoring", Arch Intern Med, vol. 167, No. 17 (Sep. 24, 2007) pp. 1869-1874.

Song et al., "Alveolar Hemostatis in Patients with Species-Specific Bacterial-Mediated Ventilator-Associated Pneumonia", Crit Care Med., Editorial, vol. 35, No. 2 (2007) pp. 652-653.

Sube et al., "Validation of a Modified Early Warning Score in Medical Admissions", Q J Med, vol. 94, (2001) pp. 521-526.

Tarassenko et al., "Integrated Monitoring and Analysis for Early Warning of Patient Deterioration", British Journal of Anesthesia, vol. 97, No. 1 (2006) pp. 64-68.

Teasdale et al., "Revisiting the Glasgow Coma Scale and Coma Score", Intensive Care Med, vol. 26 (2000) pp. 153-154.

Tirschwell, David, "Improved Prediction of Awakening or Nonawakening in Severe Anoxic Coma Using Tree-Based Classification", Crit Care Med., Editorial, vol. 34, No. 5 (2006) pp. 1573-1574.

Tsai, Amy G., "Can the Effects of Vasoactivity of Molecular Hemoglobin-Based Plasma Expanders be Ignored", Crit Care Med., Editorial, vol. 34, No. 5 (2006) pp. 1566-1567.

van der Voot, P.H.J., "Diagnostic and Scientific Dilemma: The Ischemic Bowel", Crit Care Med., Editorial, vol. 34, No. 5 (2006) pp. 1561-1562.

van der Voot, P.H.J., "The Incomplete Puzzle of Vasoactive Medication in (Abdominal) Sepsis", Crit Care Med., Editorial, vol. 34, No. 5 (2006) pp. 1565-1566.

Van Venrooij et al., "International Prostate Symptom Score and Quality of Life Assessment Versus Urodynamic Parameters in Men with Benign Prostatic Hyperplasia Symptoms", The Journal of Urology, vol. 153 (May 1995) pp. 1516-1519.

Wagner, Douglas P., Ph.D., "What Accounts for the Difference between Observed and Predicted?", Crit Care Med., Editorial, vol. 34, No. 5 (2006) pp. 1552-1553.

Wang et al., "Is Inter-Alpha Inhibitor Important in Sepsis", Crit Care Med., Editorial, vol. 35, No. 2 (2007) pp. 634-635.

Watkinson et al., "A Randomised Controlled Trial of the Effect of Continuous Electronic Physiological Monitoring on the Adverse Event Rate in High Risk Medical and Surgical Patients", Anesthesia, vol. 61 (2006) pp. 1031-1039.

Webster, Nigel R., "Monitoring the Critically Ill Patient", J.R. Coll. Surg. Edinb., vol. 44 (Dec. 1999) pp. 386-393.

Weisberg, Lawrence, S., "Sic Transit Acetylcysteine?", Crit Care Med., Editorial, vol. 35, No. 2 (2007) pp. 644-645.

Werdan, Karl, MD "Immunoglobulin Treatment in Sepsis—Is the Answer 'No'?", Crit Care Med., Editorial, vol. 34, No. 5 (2006) pp. 1542-1544.

Winters et al., "Rapid Response Systems: A Systematic Review", Crit Care Med, vol. 35, No. 5, (2007), pp. 1238-1243.

Winters et al., "Rapid Response Teams-Walk, Don't Run", JAMA, vol. 296, No. 13, (Oct. 4, 2006), pp. 1645-1647.

Young, G. Bryan, "Intensive Care Unit/Critical Illness Myopathy: Toward a Unifying Hypothesis", Crit Care Med., Editorial, vol. 35, No. 2 (2007) pp. 628-629.

Zimmerman et al., "Acute Physiology and Chronic Health Evaluation (APACHE) IV: Hospital Mortality Assessment for Today's Critically Ill Patients", Crit Care Med, vol. 3, No. 5 (2006) pp. 1297-1310.

PCT International Search Report based on PCT/US06/06467 dated Sep. 17, 2001.

PCT International Search Report based on PCT/US07/022054 dated Apr. 2, 2008.

International Search Report based on PCT/US09/061478 dated Dec. 10, 2009.

Office Action in U.S. Appl. No. 11/974,696 mailed May 25, 2010.

Reintam et al., "Gastrointestinal Failure in Intensive Care : a Retrospective Clinical Study in Three Different Intensive Care Units in Germany and Estonia" BMC Gastroenterology © 2006.

"Braden Scale for Predicting for Predicting Pressure Sore Risk" © Barbara Braden and Nancy Bergstrom 1988.

Cathy, Jones "Glasgow Coma Scale" The American Journal of Nursing, vol. 79, No. 9 (Sep. 1979), pp. 1551-1553.

Supplementary European Search Report based on PCT/US06/06467 dated Jul. 21, 2009.

Office Action in U.S. Appl. No. 11/974,696 mailed Jul. 1, 2009.

Antman et al., "The TIMI Risk Score for Unstable Angina/Non-ST Elevation MI—A Method for Prognostication and Therapeutic Decision Making," JAMA, 284(7), pp. 835-842 (Aug. 16, 2000).

Braden, "The Relationship Between Stress and Pressure Sore Formation," Ostomy/Wound Management, 44, pp. 26S-37S (Mar. 1, 1992).

Egevad et al., "Prognostic Value of the Gleason Score in Prostate Cancer," BJU International, 89(6), pp. 538-542 (Apr. 9, 2002).

Marshall et al., "Multiple Organ Dysfunction Score: A Reliable Descriptor of a Complex Clinical Outcome," Critical Care Medicine, 23(10), pp. 1638-1652 (Oct. 1, 1995).

Pollack et al., "PRISM III: An Updated Pediatric Risk of Mortality Score," Critical Care Medicine, 24(5), pp. 743-752 (May 1, 1996).

Rees, "Early Warning Scores," Update in Anaesthesia, World Anaesthesia, 17(10), pp. 30-33 (2003).

Ryan et al., "Setting Standards for Assessment of Ward Patients at Risk of Deterioration," British Journal of Nursing, 13(20), pp. 118-1190 (Nov. 2004).

Subbe et al., "Effect of Introducing the Modified Early Warning Score on Clinical Outcomes, Cardio-Pulmonary Arrests and Intensive Care Utilisation in Acute Medical Admissions," Anaesthesia, 58(8), pp. 797-802 (Jul. 14, 2003).

Office Action in U.S. Appl. No. 11/974,696 mailed Feb. 2, 2010.

Office Action in U.S. Appl. No. 11/974,696 mailed Jun. 10, 2011.

PCT International Search Report based on PCT/US2006/06467 dated Sep. 14, 2007.

* cited by examiner

SYSTEM AND METHOD FOR IMPROVING HOSPITAL PATIENT CARE BY PROVIDING A CONTINUAL MEASUREMENT OF HEALTH

RELATED APPLICATION

This application is related to and claims the benefit of priority from U.S. Provisional Patent Application No. 60/657,365, filed on Feb. 28, 2005, the entirety of which is incorporated herein by reference.

FIELD OF THE INVENTION

The present invention relates to a system and method for improving hospital patient care. More particularly, the present invention relates to a system and method for providing a continual measurement and display of each patient's health.

BACKGROUND

One of the major problems in delivery of effective medical treatment in hospitals is the quality and continuity of patient care. A typical patient, undergoing a serious procedure in a hospital, may easily see five or more physicians during a stay, and also many nurses and other supporting personnel. Maintaining a complete medical record for each patient ("charting") swallows huge amounts of nursing time without providing any guidance to the medical staff on how to improve the patient's care. The present state of the art in medical care within hospitals makes very little use of the medical record, which is so bulky and awkward that it can only be quickly perused by doctors on their rounds. Such reading of the chart makes it almost impossible to evaluate treatment modalities, or to detect a patient's declining health in time for intervention (before a crisis).

During a week's hospital stay, each patient may see many doctors and many nurses. This makes it extremely difficult to provide continuity of care. Every different caregiver must understand the medical record to give the patient optimum care, but the form and content of present-day medical charting provides no help. Each subsequent physician, whether a consultant or a shift replacement, is ill-prepared by current methods to obtain a correct overall medical status of the patient, thus posing a danger to the continued care of the patient, particularly in the recovery stages after serious operations For example, an attending physician, while making rounds in a hospital, may stop in on a patient, see that the patient has good color and is sitting up in bed, and thusly satisfied, goes on to his next appointment. However, if that patient had been walking up and down the corridors two days ago, and now cannot get out of bed, there is a problem. The patient may be experiencing a major and potentially life-threatening complication.

The essence of this problem is that, although all the medical information is recorded, it is not easily understood. After just a few days in the hospital, a patient may have twenty or even one hundred pages in their hospital record, including physician progress reports, nursing evaluations, records of vital signs, test results, heart monitoring information, and so on. However, even if every doctor and nurse who saw the patient were fully aware of the material in this record, it would not be enough to allow for the best medical care because it is very difficult to detect trends in such voluminous data.

The result of this arrangement has been to allow a number of patients in recovery, post-operation or procedure, to deteriorate to the point of medical crisis before addressing their problems. This causes a serious drain to the resources of the hospital, and much unnecessary pain and suffering, even death. It is particularly bothersome because many of the conditions that lead to such crises can easily be avoided if the failing condition of a patient were discovered hours or days earlier.

One thing that a few hospitals have done is to employ an Early Warning System (EWS) as a means for deciding whether a patient needs to be transferred to the ICU. Other hospitals have developed a Modified Early Warning System (MEWS). Both existing systems typically use a small number of factors such a pulse, blood pressure, temperature, and respiratory rate. For each factor, a partial score is given, and all of these are then tabulated into a total score, which in turn is expressed as a binary recommendation: whether or not to move the patient into the ICU; no other action is suggested, no other information is obtained.

Such systems determine a patient's need to be transferred to the ICU by providing an emergency alert. However, these systems do not provide assistance to the doctor or nurse in helping to anticipate and thereby avoid medical crises, nor are they helpful to the clinical researcher in evaluating the efficacy of procedures and treatments. They convey no health trend information. Also, they are limited in the number of factors analyzed and thus are not very sensitive to general health conditions. For example, in the above-described example of a patient sitting up and alert in bed, this type of evaluation completely misses the patient's declining health. Because the patient still does have acceptable vital signs, he is not moved to the ICU, and neither the EWS, nor the MEWS, would generate an alert. However, if during the two previous days, this same patient had been walking around the hospital halls, but is now not able to rise from a bed, an important medical decline has happened, possibly one that will lead to a medical crises if not attended to, even though his major vital signs are still acceptable. Our invention addresses these omissions, providing new continual, sensitive tools for improving medical care.

OBJECTS AND SUMMARY

The present invention overcomes the drawbacks associated with the prior art by providing a system and method for continually tracking the health of a patient in a hospital. One advantage of such a system is, in general, to allow physicians and nurses and clinical researchers to provide more effective health care for each patient, especially those spending several days in a hospital. A second advantage is that hospitals can avoid errors and reduce crisis management by using the invention's capability to detect trends in a patient's health before the patient reaches a crisis point. Recognizing a serious decline soon enough to administer proper treatment is a life-saving benefit. A third advantage is that such a system gives physicians and nurses a way in which to get the "big picture" of a patient's condition and absorb in a glance perhaps 100 pages of a patient's medical records. This deeper understanding, along with this new capability to detect health trends, both short-term (over the space of hours), and long-term (over the space of days), is extremely important in delivery of effective medical care. A fourth advantage is to enable an entirely new field of scientific study, where medical and surgical treatments can be evaluated by the new measurements provided by this invention.

The present invention generates a new measurement of health, herein termed the patient "Health Score" which is continually plotted and displayed to show each patient's medical progress during his hospital stay. This invention may prove to be a vital aid for improving the quality and continuity of medical care.

To this end the present invention provides a system for improving hospital patient care by generating a Health Score. The system includes an interface module for receiving incoming medical data from a patient, a transformation module for transforming each of the medical datum into a transformed Health Score value, and a combination module for combining the transformed Health Score values corresponding to each of the medical datum into a single Health Score. A presentation and comparison module displays the Health Score as a Health Score plot over a predetermined time frame, such that a user may identify health trends in a patient by evaluating said Health Score plot.

BRIEF DESCRIPTION OF THE DRAWINGS

For the purpose of illustrating the invention, there are shown in the drawings several forms, which are presently preferred, it being understood, however, that the invention is not limited to the precise arrangements and instrumentalities shown.

DETAILED DESCRIPTION

In one embodiment of the present invention, a Health Score system 10 is provided for generating and presenting a Health Score chart. The newly invented Health Score is a medical reference "figure-of-merit" that is used by a physician or nurse to track the patient's health before, during or after a medical procedure or illness, in order to assist in preventing that patient from reaching a health crisis. When used in this manner, the Health Score chart enables the attending physicians and nurses to detect trends in the patient's health over time, particularly in evaluating post-operative recovery in the hospital. It also provides a statistically significant "outcome" for both clinical studies and retrospective studies of the relative efficacies among various surgical procedures or techniques, and among medical treatments and drugs.

In addition to short term intensive use of the Health Score system 10, a similar modified form may be used on a long term basis by regular general practitioners or other health care facilitates such as nursing homes. For example, as it stands, yearly physicals are usually accompanied by a series of medial measurements of the patient. Entering such data in Health Score system 10 may be useful in spotting long term declining health trends, even if none of the particular medical conditions have reached a crisis level.

Figure 1:
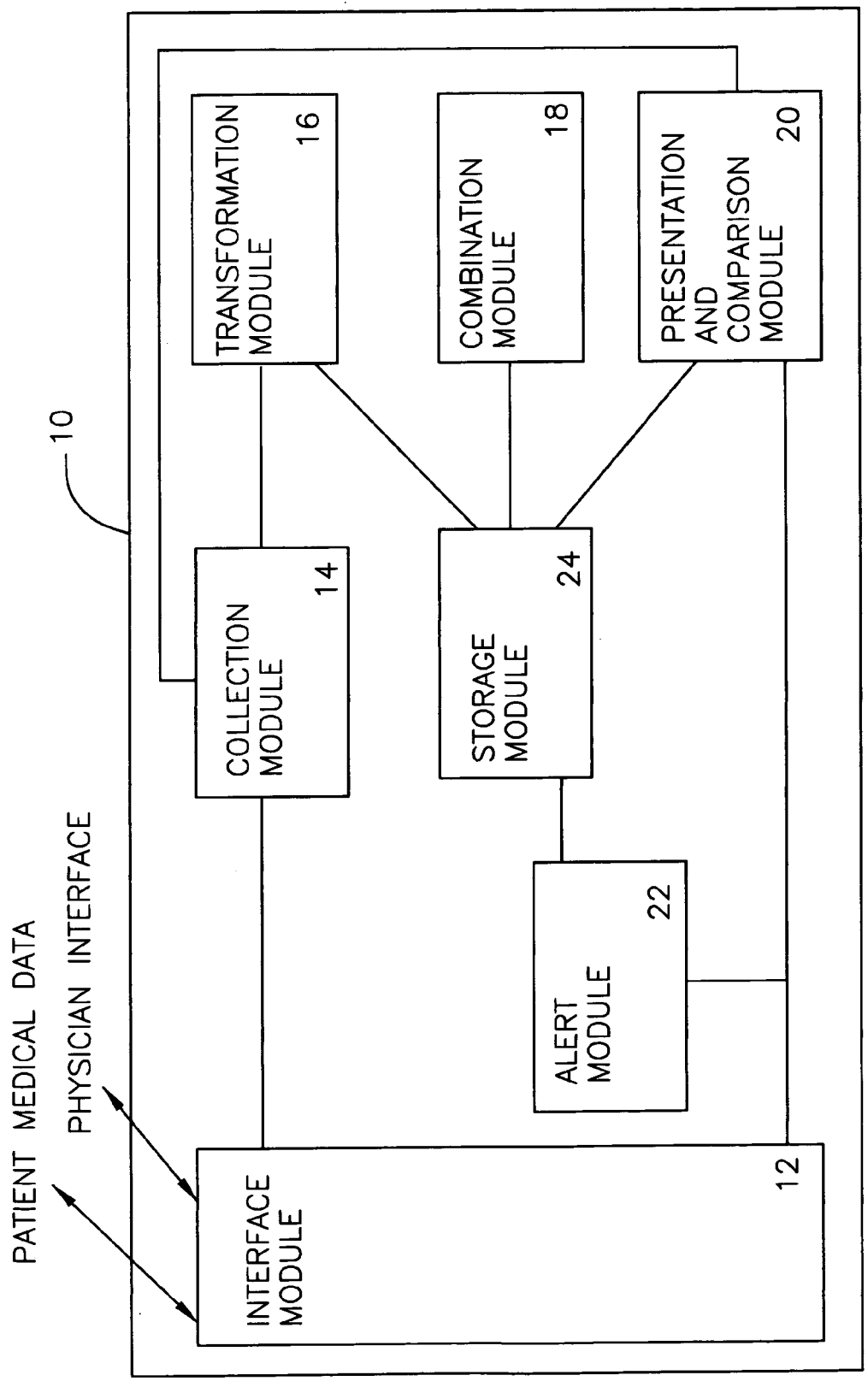
FIG. 1 is a logical diagram of the Health Score system, in accordance with one embodiment of the present invention.

To generate and present the Health Score, as illustrated in FIG. 1, system 10 maintains an interface module 12, a collection module 14, a transformation module 16, a combination module 18, a presentation and comparison module 20, an alert module 22, and a storage module 24.

Interface module 12 is configured to obtain raw medical input, either directly from patient monitoring devices, or from attending physicians or nurses. Collection module 14 collects the raw medical data from interface module 12, and further collects additional material from storage module 24, including the patient's historical medical data as well as other required general medical data (optional statistics). The raw medical data is transmitted to transformation module 16, and the stored and historical medical data is sent to presentation and comparison module 20.

Transformation module 16 receives incoming raw medical data and converts this data into a usable format for generating the patient's Health Score. Transformation module 16 converts raw medical data into a form that will allow different types of data to be combined. The transformed data is then sent to combination module 18, which in turn generates a patient's Health Score, using a predetermined algorithm.

Presentation and comparison module 20 receives the calculated Health Score and prepares a Health Score chart 100, plotting the patient's Health Score as a function of time. Alert module 22, generates an alarm for the attending physicians and nurses when a problem is detected with a patient's Health Score chart 100. Such problems are alerted when the Health Score of a patient descends below an acceptable threshold, determined in advance by system 10 or set by the attending physician, or if a downward trend is detected. Storage module 24 is configured to store and retrieve Health Score information at various times during the Health Score generation and presentation procedure.

It is understood that the above list of modules is intended only as a sample of the logical organization of modules within system 10. For example, many of the modules may be combined with one another or subdivided and separated according to their function. Any similar Health Score system, employing similar logical modules to obtain a Health Score is also within the contemplation of the present invention.

Furthermore, it is noted that the modules of system 10, illustrated in FIG. 1, are to show their logical relationship to one another. However, this is not intended to limit the physical construction of such a system. For example, system 10 may be employed on a single larger computer or on a series of smaller computers, possibly with different components residing within different geographical locations, such as the use of an off-site storage module 24. Any similar health care system 10, employing similar modules to generate a Health Score alert, is within the contemplation of the present invention.

Figure 2:
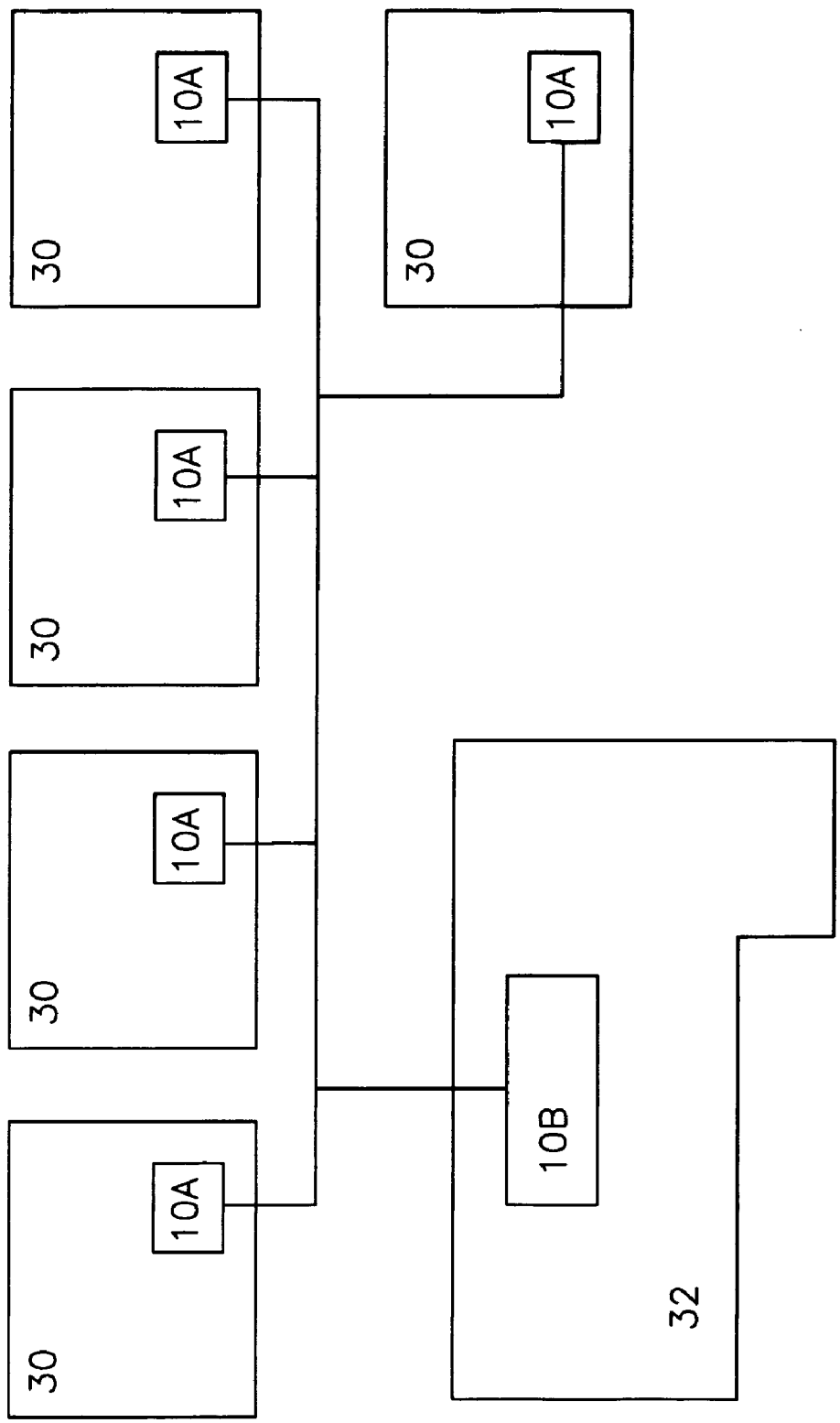
FIG. 2 is an installation arrangement of the Health Score system as shown in FIG. 1, in accordance with one embodiment of the present invention.

FIG. 2 gives a typical example of an arrangement for system 10, showing five patient recovery rooms 30, in a typical hospital with a central nursing station 32 that is monitored 24 hours a day. System 10 has a local terminal 10A in each of the five patient rooms 30 and a main terminal 10B at nursing station 32.

Figure 3:
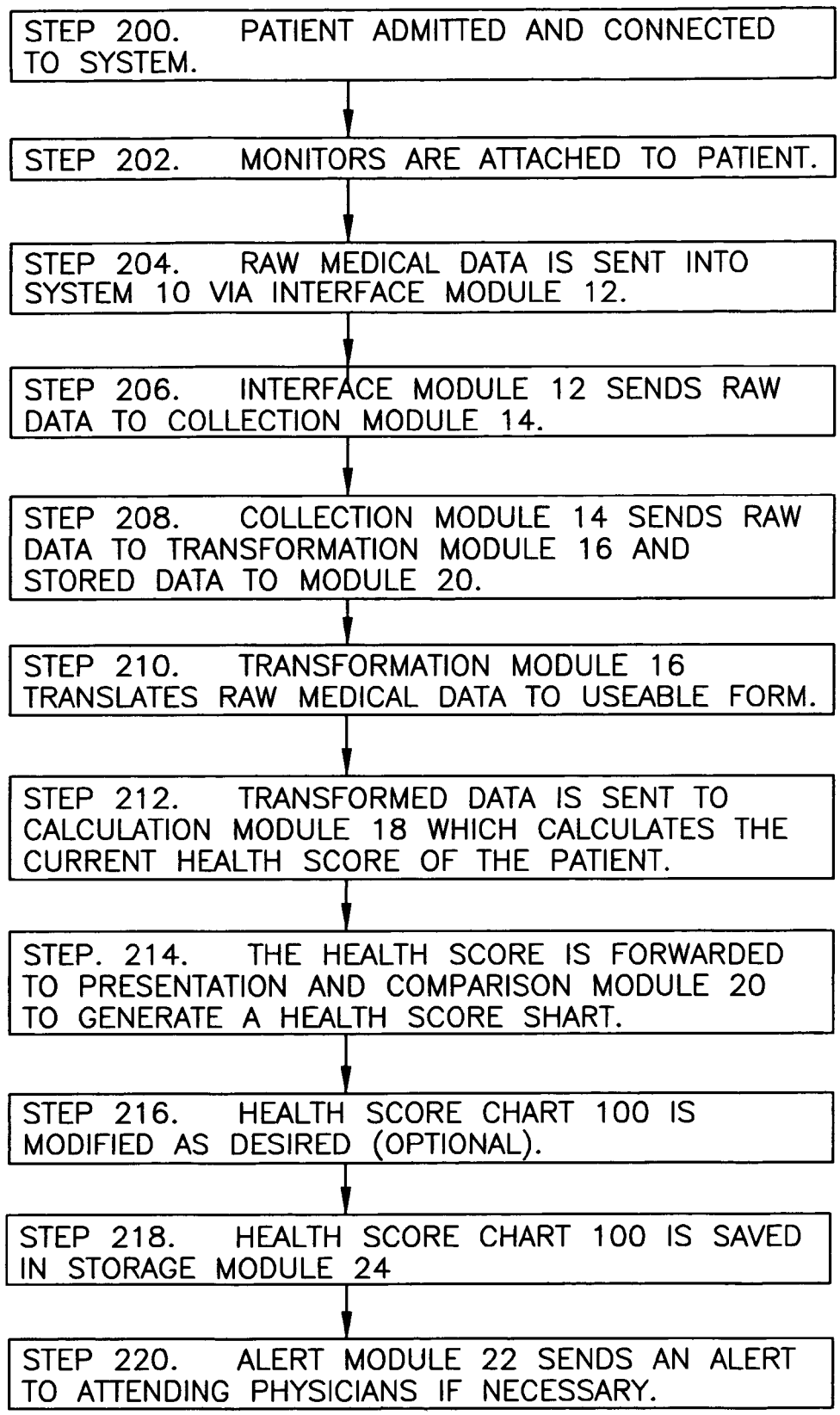
FIG. 3 is a flow chart of the generation of a Health Score chart, using the Health Score system illustrated in FIG. 1, in accordance with one embodiment of the present invention.

FIG. 3 is a flow chart outlining the process for generating and presenting a patient's Health Score via system 10. In step 200, a patient is admitted for a particular illness or surgical procedure and is subsequently connected to system 10. At step 202, various medical devices/monitors for obtaining the pertinent raw medical data are attached to the patient, such as blood pressure monitors, heart rate monitors, etc.

At step 204, interface module 12 begins obtaining the pertinent raw medical data about the patient and imports this data into system 10. Some data is obtained directly from the attached medical devices or from electronic medical records. Other data may be entered into the system by an attending physician or nurse. At step 206, this data is sent to collection module 14. At step 208, collection module 14 further obtains any necessary past medical data, most importantly the past Health Scores of the same patient. The raw data is transmitted to transformation module 16, and the historical data is sent to presentation and comparison module 20.

Next, at step 210, transformation module 16 transforms the raw patient medical data into a usable format, so that all of the disparate forms of medical data can readily be compiled with one another. At step 212, the transformed medical data is sent to combination module 18, which converts that raw transformed medical data into a Health Score using a predetermined algorithm. At step 214, the Health Score is transmitted to presentation and comparison module 20, which uses the current Health Score, as well as historical data from storage module 24 (past Health Scores), to generate a Health Score chart 100.

Figure 4:
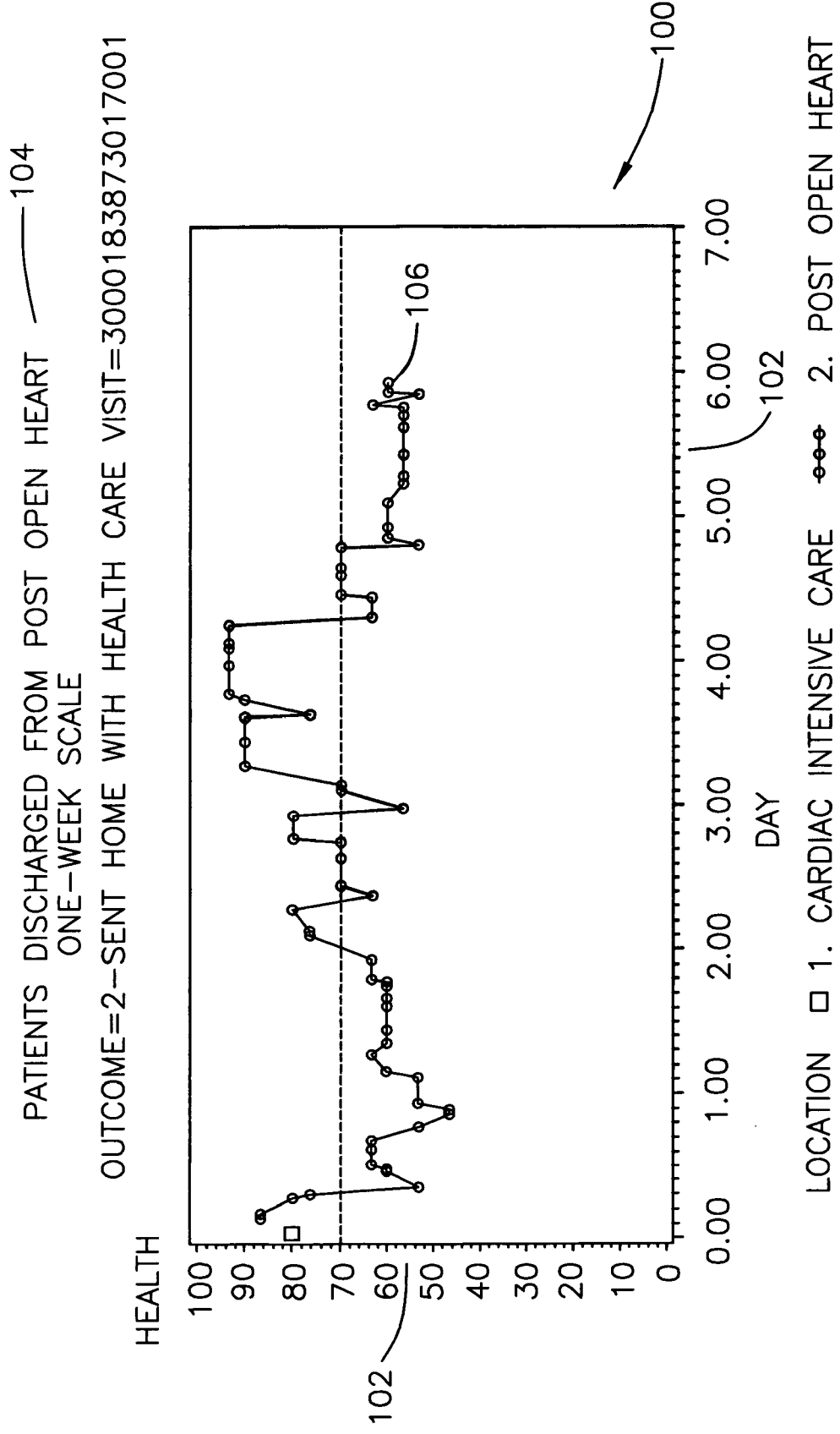
FIG. 4 is a sample Health Score chart, in accordance with one embodiment of the present invention.

A sample Health Score chart 100 is shown in FIG. 4, plotting a patient's Health Score, calculated by system 10 as a function of time. Chart 100 includes scale markings 102 and label material 104 and a Health Score plot 106. This chart 100 shows a sample Health Score plot 106 for a patient recovering from open-heart surgery, for 6 days. Initially the recovery was going well, but at approximately the beginning of the fourth day, health deteriorated. A more detailed description of the contents and evaluation of a Health Score chart 100 is included below.

At step 216, after Health Score chart 100 has been generated, presentation and comparison module 20 may modify and display the Health Score chart 100 to healthcare providers, via interface module 12 of system 10. At step 218, presentation and comparison module may further save any necessary information to storage module 24.

Finally at step 220, if the Health Score, according to plot 106, falls below a predetermined threshold, alert module 22 informs the healthcare providers, either through interface module 12 or via some other alarm, that the patient is in need of attention.

It is noted that the above list of steps for generating Health Score chart 100 via system 10 is intended only to show an exemplary step-by-step process. For example, several of the steps may be combined with one another or possibly one step may be divided into a number of subroutines. Any similar process using steps to create a Health Score chart on a similar system is also with in the contemplation of the present invention.

Turning now to a more detailed description of the various modules of system 10, interface module 12 receives raw medical data input at step 204, and transmits it to the various collection and processing modules 14, 16, 18, 20, 22 and 24 of system 10, at step 206. Typically, the input may include any number of the medical statistics that are used to generate the Health Score produced by system 10. Interface module 12 of system 10 may be as simple as a keyboard and monitor, used for manual entry of patient data. Furthermore, it may additionally include a set of automated electrical instruments such as pulse clips, automated blood pressure devices, blood oxygen measuring devices, fluid monitoring devices or any other standard medical measuring device, attached either by wire or remotely to interface module 12.

In addition to providing an interface for receiving medical data on the patients, interface module 12 may also be configured to present a means for users, such as doctors or nurses, to update, modify or review the patient's Health Score at step 216. Furthermore, interface module 12 may also be employed by alert module 22 at step 220 to alert the healthcare providers that alert module 22 has detected a threshold breach, which is explained in greater detail below Collection module 14 is coupled to interface module 12 for receiving the various raw patient data at step 206. Collection module 14 accepts this data from various ports, including interface module 12 as well as other programs, such as electronic medical records (EMR), and stores this data in storage module 24. Thus, in addition to the raw physical patient data and physician/nurse input obtained from interface module 12, collection module 14 further collects and organizes all of the data necessary to generate and maintain the Health Score chart 100 of the patient, including collection of historical data, performed at step 208.

In one example of generating a Health Score chart 100, the necessary patient data that must be collected by collection module 14 of system 10 may include: diastolic blood pressure, systolic blood pressure, temperature, pulse, respiration rate, a pain score, skin breakdown score, EKG pattern, and a set of nursing assessments. Nursing assessments may include: respiration, pain, cardiac, gastrointestinal, genitourinary, nutrition, musculoskeletal, skin, neurological, psychosocial, peripheral vascular, and safety (likelihood of falling). Thus, collection module 14 obtains both past and present data necessary for the patient on each of the categories to form Health Score chart 100.

Transformation module 16 is configured to transform each of the pieces of medical data obtained from collection module 14 into a numerical quantity at step 210. The transformation performed by module 16 may include any number of mathematical or logical operations. Transformations may also take multiple inputs to produce a single transformed output. Multiple inputs may include historical data for this patient or for any given class of patients. For example, if the patient's pulse is greater then one standard deviation above that expected for a certain group of patients at this stage of their recovery, then the value of "High Pulse" is one, otherwise it is zero. An example of a transformation for diastolic blood pressure (TDBP) would be:

if diastolic blood pressure (DBP)<50, then TDBP=2;
   if DBP>50 and DBP<90, then TDBP=0;
   if DBP>89 and DBP<100, then TDBP=1;
   if DBP>99 then, TDBP=2.

In this case, either very low values of diastolic blood pressure (less than 50), or high values of diastolic blood pressure (greater than 99), are considered dangerous.

Another example of a transformation may be for a nursing assessment. For example, if the respiration assessment equals "met standards" then the transformed respiration rate equals zero. If the nursing assessment for respiration equals "did not meet standards" then the transformed respiration rate equals one.

Thus, transformation module 16, after receiving raw data from collection module 14, processes the data and transforms them into numbers for use in generating a Health Score for the patient.

The following serves as an example of a list of typical conversions of raw medical data into numerical form ("transformed numbers") by transformation module 16, for use by system 10 in developing a patient Health Score:

if diastolic blood pressure<50 then Transformed Diastolic BP=2
diastolic between 50 and 89, then . . . 0
diastolic between 90 and 99, then . . . 1
diastolic>99, then . . . 2
all nursing assessments . . . Met=0 . . . or Not Met=1
multiply cardiac, neurological, pain, peripheral vascular, psychosocial, respiratory and skin/tissue assessments by 2
if Braden score<18, then . . . 1
if Braden score greater or equal to 18, then . . . 0
if systolic blood pressure<70, then . . . 3
if systolic>69 and <81, then . . . 2
if systolic>80 and less than 101, then . . . 1
if systolic>100 and <200, then . . . 0
if systolic>199, then . . . 2
if heart rate<40, then . . . 2
if heart rate>39 and <51, then . . . 1
if heart rate>50 and <101, then . . . 0
if heart rate>100 and <111, then . . . 1
if heart rate>110 and <130, then . . . 2
if heart rate>129, then . . . 3
if respiration<9, then . . . 2
if respiration>8 and <15, then . . . 0
if respiration>14 and <21, then . . . 1
if respiration>20 and <30, then . . . 2
if respiration>29, than . . . 3
if temperature<95, then . . . 2
if temperature>94 and <101.1, then . . . 0
if temperature greater or equal to 101.1, then . . . 2
If the monitored heart pattern is "atrial fibrillation", "sinus rhythm", "sinus tachycardia" or "paced" then . . . 1
If the monitored heart pattern is "sinus bradycardia" then . . . 2
If the monitored heart pattern is "atrial flutter" OR "heart block" then . . . 3
If the monitored heart pattern is "junctional rhythm" then . . . 4
If the monitored heart pattern is "ventricular tachycardia" then . . . 5
Or if the monitored heart pattern is "ventricular fibrillation" then . . . 5.

These conversions of patient data into numbers are done solely for the purpose of example. It is understood that any conversion of raw medical data into a useable form for further calculation within the context of system 10 is within the contemplation of the present invention.

The above conversions of medical data into scaled numbers is geared to assessment of negative factors. However, it is understood that positive assessments may be included too, resulting in "negative" scaled numbers, that would show a positive affect on the Health Score. For example, transformation module 16 may give a negative scaled number in the event that heart rate or lung capacity or other such medical data is not only OK, but is in fact at an ideal state.

Combination module 18 is configured to take the transformed quantities from transformation module 16, apply weighting modifiers, and to combine them, and then to scale them onto a range, such as a score between 0 and 100, at step 212. This score, generated by combination module 18, is based on the various health factors measured and transformed above, the resulting score being a relative overall Health Score of the patient being monitored.

An example of a combination Health Score generated by combination module 18, using the "transformed numbers" (as described above) generated by transformation module 16 of system 10, may be:

Part 1

"Health Sum"=Diastolic Blood Pressure+Temperature+Respiration+Systolic Blood Pressure+Heart Rate+Braden Score+Cardiac Assessment+Food Assessment+Gastrointestinal Assessment+Genitourinary Assessment+Heart Rhythm+Musculoskeletal Assessment+Neurological Assessment+Pain Score+Pain Assessment+Peripheral Vascular Assessment+Psycho-Sociological+Respiratory Assessment+Safety/Fall Assessment+Skin/Tissue Assessment Part 2

Health Score=100*(30−"Health Sum")/30

Based upon the above formulae, a sample calculation of a patient's Health Score could be performed by transformation module 16 and combination module 18, if the collection module 14 of system 10 found the following raw medical data:

Diastolic Blood Pressure of 95=1
Negative nursing cardiac assessment=2
Negative nursing respiratory assessment=2
Braden Score of 18=0
Systolic Blood Pressure of 202=1
Heart Rate of 100=1
Respiration Rate of 14=0
Temperature of 98=0
Heart Rhythm of sinus bradycardia=2
"Health Sum"=(totaling of all above)=9

Health Score=100*(30−"Health Sum")/30=100*(30−9)/30=70

Such transformations and calculations are intended only to be a simple example of determining a Health Score, as performed by system 10. However, it is in no way intended to limit the possible methods of calculating the score. For example, not all measured raw medical data need to be incorporated into a Health Score. The attending physician may wish to generate the score using only limited data to prevent non-essential medical data from significantly altering the Health Score.

Another example would be to include the use of weighting factors (2 times, 3 times, etc.) that can be added or multiplied to certain transformed numbers, such as the respiratory factors, when a particular patient is recovering from a lung-based ailment such as pneumonia. Likewise, similar weighting factors can be added to the transformed scores of heart rate, heart rhythm, systolic and diastolic pressure for patients with heart ailments. It is understood that any number of modifications introduced into a similar combination module 18 within a similar system 10 for generating a Health Score is within the contemplation of the present invention.

Presentation and comparison module 20 of system 10 is configured to import the various data components compiled by combination module 18 and to create a Health Score chart 100 for the patient at step 214, and display it via interface module 12 of system 10, or on an existing medical information system, such as the hospital's pre-existing computer system. As discussed above, FIG. 4 illustrates a sample Health Score chart 100 generated by system 10 using the above-described modules. Additional functions of comparison module 20 are shown below which edit, modify or otherwise present various versions of Health Score chart 100, performed by system 10 at step 216.

Health Score chart 100 is for displaying the Health Score of a patient at particular times, and more importantly, is for detecting trends in a patient's health. Thus, Health Score chart 100 includes a number of Health Score assessments taken frequently, both at periodic (e.g. every 15 minutes, or every 3 hours), or at irregular intervals. This generates the Health Score chart 106 as shown in FIG. 4, plotting the patient's Health Score versus time as set by scales 102.

For example in FIG. 4, the Health Score of the patient is computed ten times a day, approximately every 2 hours over the course of the six-day post-operative stay. During the first four days, the patient progressed from an average Health Score in the low 60s to the high 80s. But shortly thereafter, at the beginning of the fourth day, the patient's score began to decline back into the 60s range.

It is at this particular moment, at the beginning of the fourth day, that the Health Score chart 100 can prove to be a critical tool for medical care. If an attending physician were to see this patient at the end of day 4 without the Health Score chart, the patient's vital statistics would show a person of decent physical health. This corresponds to the score of 70 on the health chart, which is about average health during a post-operation recovery, according to this example. Thus without the chart 100, the patient would exhibit decent health, and the attending physician would have to rely his own quick perusal of the patient's medical records.

However, with the Health Score chart 100 available, it would be obvious to a physician or nurse that something is going wrong with the patient at the end of day 4. This is a critical time for the patient, because immediate treatment may prevent a crisis. The new information conveyed by chart 100, beyond what is normally available (that the patient is currently in an acceptable state), is that: less than 1 day ago, this patient was in a much better general state of health and is currently in a state of declining health. Thus by intervening in the situation right at the beginning of day 5, the doctors were able to be stabilize the patient without further significant decline, so that he could be released from the hospital at the end of day 6.

Figure 5:
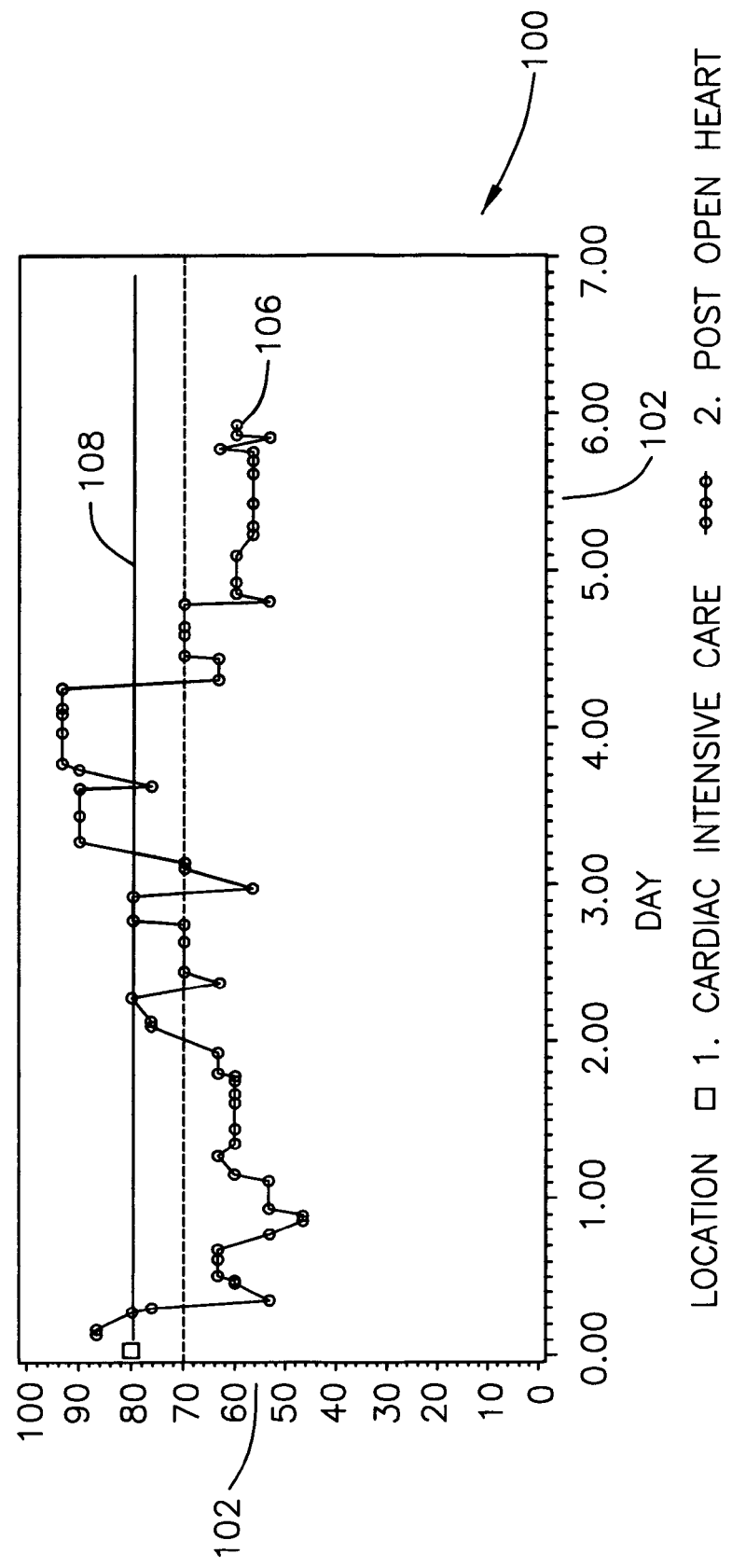
FIG. 5 is a sample Health Score chart as shown in FIG. 4 with additional pre-operation information, in accordance with one embodiment of the present invention.

Comparison module 20 may be used to generate and present pre-operation reference curves. Information from pre-operation 108 may be posted on the patient's Health Score chart 100 so as to give additional context to their condition. For example, before an operation, the patient may have exhibited a Health Score of 50. After the operation, the doctors may expect the patient to be significantly better. Since before the operation he had a Health Score of 75, we expect that, although he will go through some difficult periods during recovery, he will get back to 75 within a week. This acts as a baseline reference, to help better personalize the chart 100 to each patient. FIG. 5 shows an example of pre-operation Health Score information 108, included on a typical Health Score chart 100, with a pre-operation Health Score of 80.

Statistical reference curves 110 may also be added to Health Score chart by comparison module 20. For example, when such information is available, statistically computed average patient Health Score trajectories, for each specific procedure and initial patient condition, may be included on chart 100 next to the Health Score plot 106. This information may be stored in a storage module 24, and be imported into comparison module 20 by collection module 14. Statistical reference curves 110 may include linear information with standard deviation error bars or transformed values. If the patient is below expectation by a certain number of standard deviations, the system generates an alert using alert module 22, as discussed below.

Figure 6:
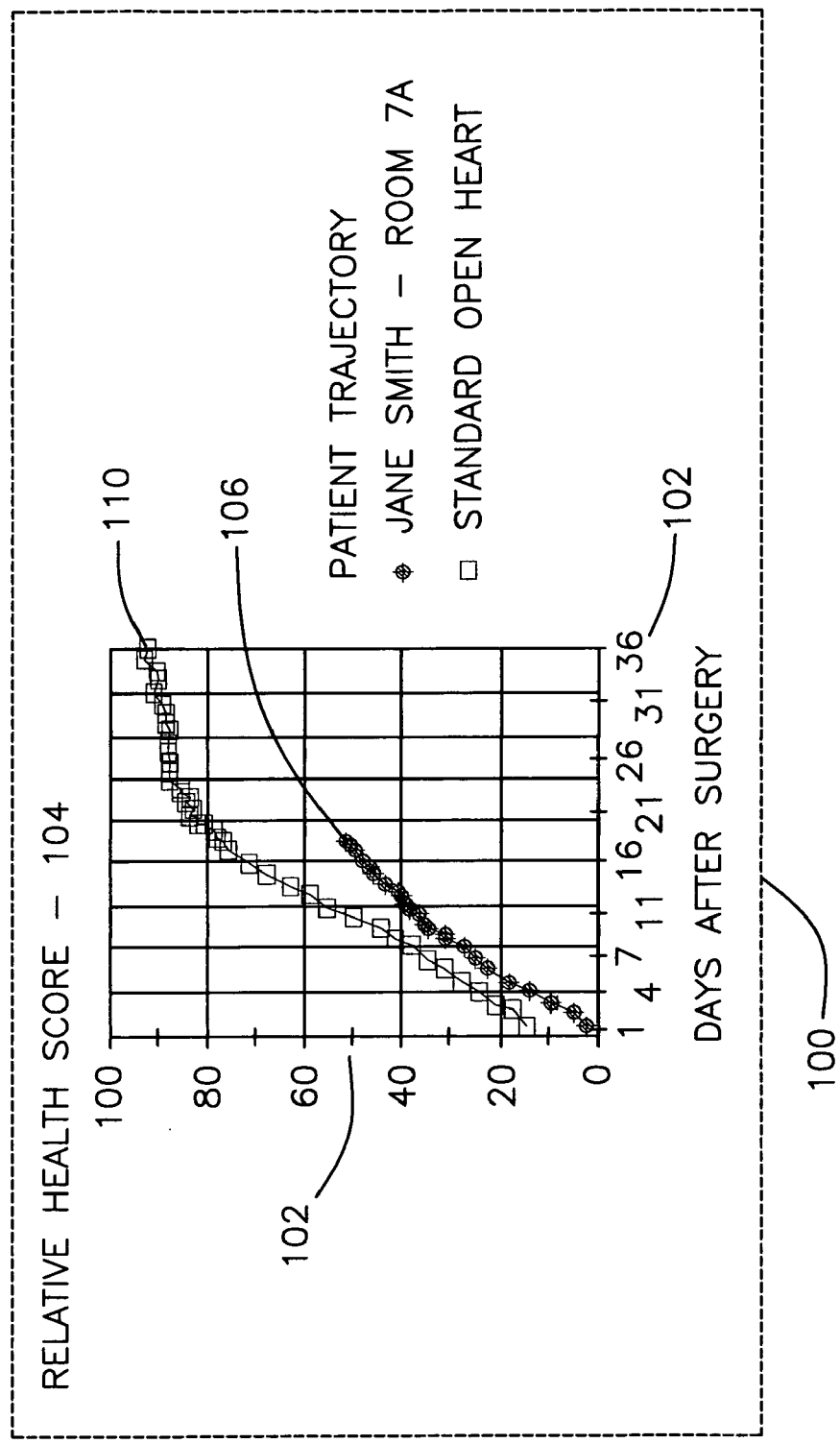
FIG. 6 is a sample Health Score chart as shown in FIG. 4 with additional statistical reference curves, in accordance with one embodiment of the present invention.

For example, in FIG. 6, on the Health Score chart 100, the line labeled "Standard Open Heart" may be a statistical reference curve 110 of the average recovery of an open-heart surgery patient of age 80. The Health Score plot 106 labeled "Jane Smith—Room 7A" is the actual Health Score representation of the recovery of Jane Smith. One sees that although Ms. Smith has steadily improved since her operation, for the last several days she has improved at a much slower rate than would be expected when compared to average (past) patients of the same age undergoing a similar procedure. Statistical reference curves 110 can be compiled from current patients or an evaluation of past patients by using their records to generate Health Score histories.

Further subdivisions can also be made for such statistical reference curves. For example, instead of having a single reference curve 110 for average open-heart patients of age 80, it can be further broken down by gender, and even further modified as to a patient's initial condition by using only patients with similar Health Scores at the time of admission into the hospital.

Figure 7:
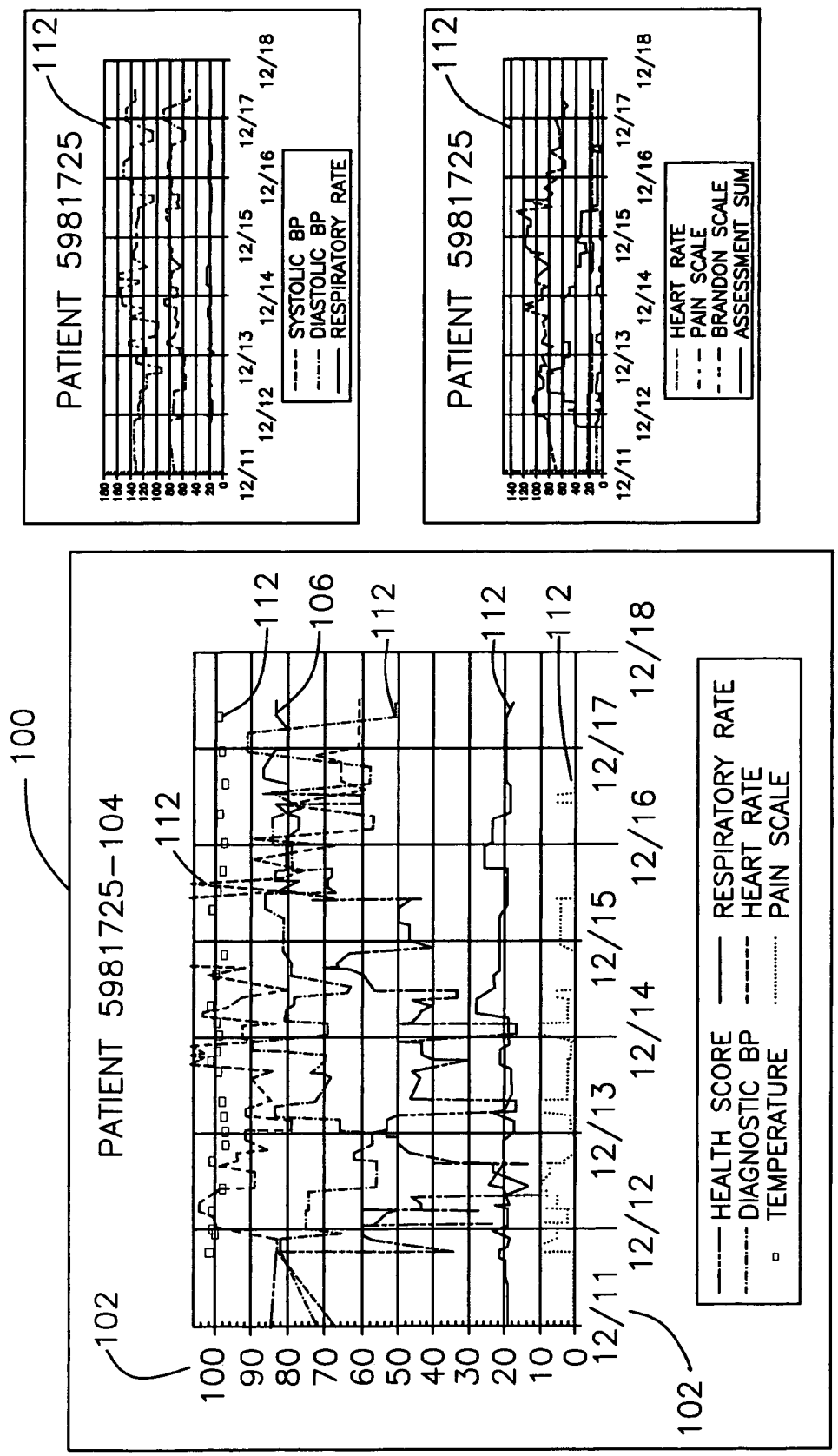
FIG. 7 is a sample Health Score chart as shown in FIG. 4 with additional principal corresponding measurement curves, in accordance with one embodiment of the present invention.

Principal corresponding measurement curves 112 may also be generated by comparison module 20 of system 10. The Health Score chart 100 provides an instant context and patient health trajectory on Health Score plot 106. It is also important for healthcare providers to have access to other direct measurements. FIG. 7 illustrates a typical Health Score chart 100 that includes these direct medical measurements 112. The measurement curves 112 may include but are not limited to: diastolic blood pressure, temperature, respiration rate, pulse, and pain score. This allows healthcare providers to detect other trends that may be affecting the Health Score and, thus, the patient.

In the example in FIG. 7, the patient has a severely reduced Health Score from December 12 through December 15. By looking at the accompanying principal corresponding measurement curves 112, it can be seen that the patient had developed a fever on the $12^{th}$ and was also dealing with Atrial Fibrillation. By the $16^{th}$ these conditions had been resolved, with a corresponding sharp increase in Health Score.

Figure 8:
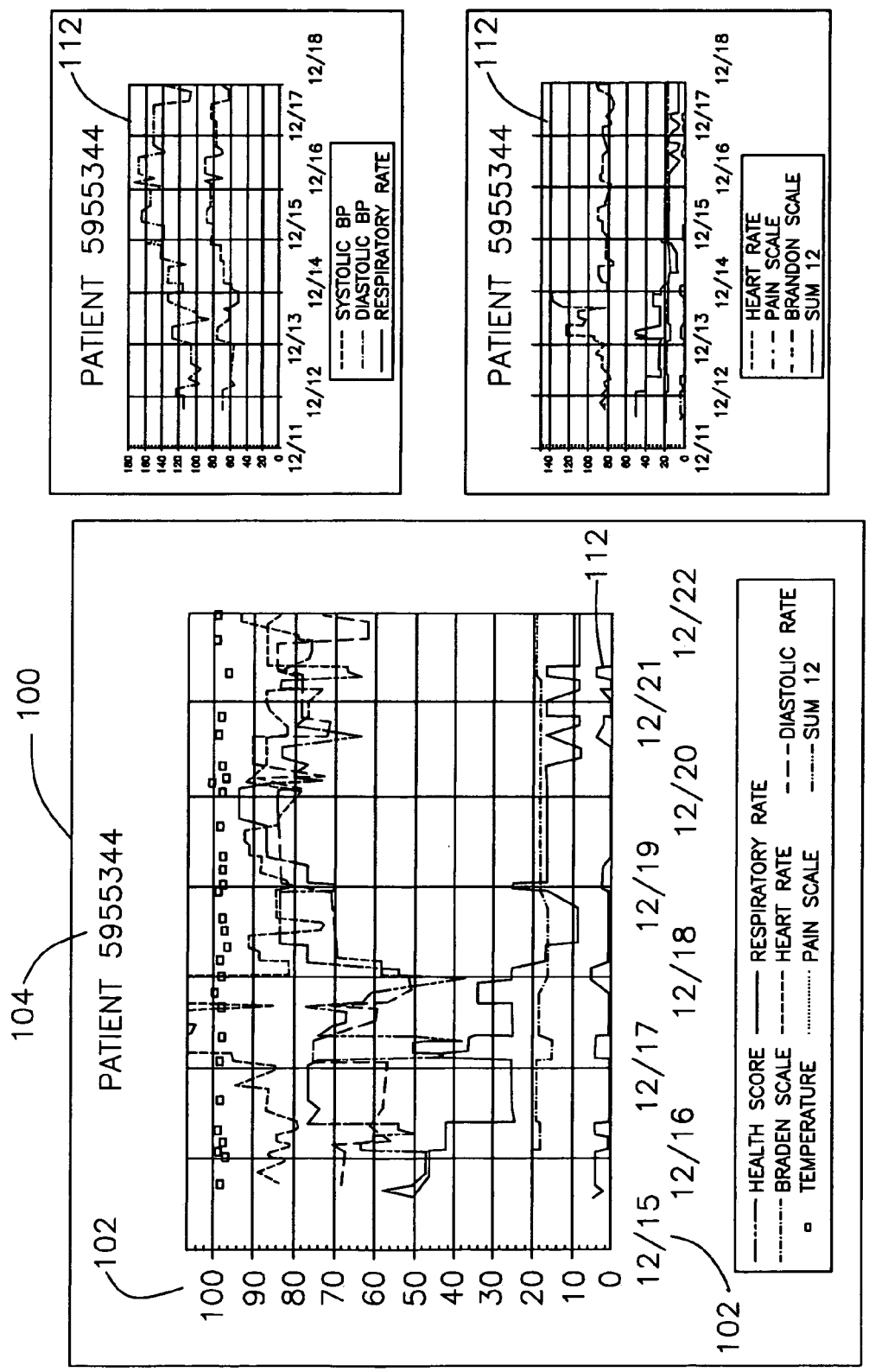
FIG. 8 is a sample Health Score chart as shown in FIG. 4 with additional principal corresponding measurement curves, in accordance with one embodiment of the present invention.

FIG. 8 is another example of adding principal corresponding measurement curves 112 to a standard Health Score chart 100. In this example, it can be seen that the Principal Corresponding Measurement curves 112 themselves are important. The line at the bottom of the Health Score chart 100 is "pain scale" which is an evaluation of the patient's pain level. It is scaled between zero and ten. This patient is experiencing significant pain almost exactly every 24 hours. This situation may be the result of a poor pain management strategy; the patient is under-medicated until he experiences a crisis, at which time a large dosage of medication is administered. Evaluation of the chart would prompt modification of this patient's pain medication frequency and dosage.

It is understood that, when using the option of adding direct medical data to the Health Score chart 100, system 10 has the ability to let the healthcare provider select which principal corresponding measurements 112 they would like to see. When the Health Score is improving or is adequate, such features may be toggled off, as they are less important in such instances. They can easily be added to chart 100 if the score on plot 106 again drops, allowing the healthcare provider, optionally, to have additional analysis tools for determining the cause of the drop.

Figure 9:
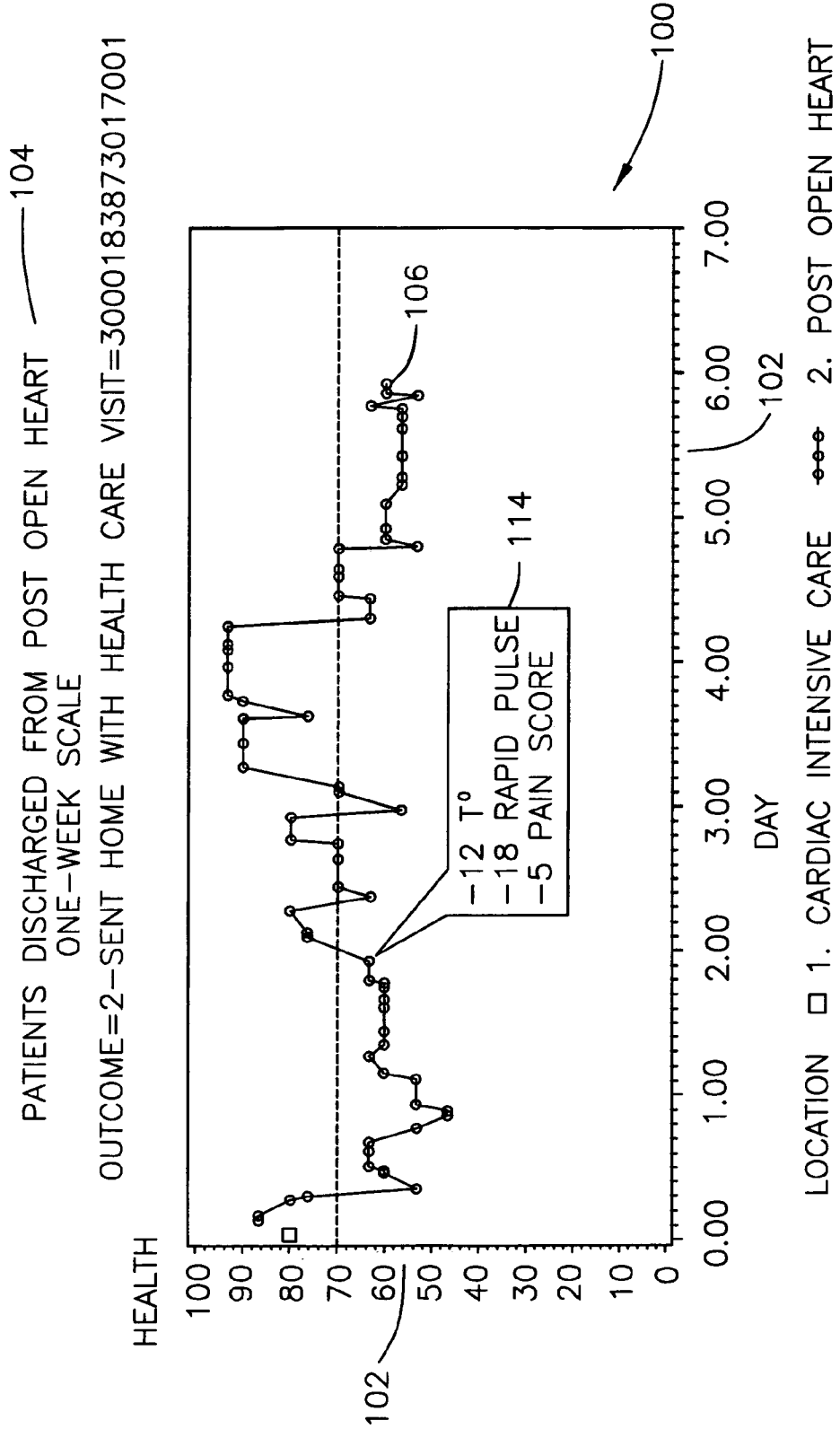
FIG. 9 is a sample Health Score chart as shown in FIG. 4 with additional component expansion window, in accordance with one embodiment of the present invention.

In another embodiment, presentation and comparison module 20 may be configured to alter Health Score chart 100, so that when a healthcare provider detects a trend in the Health Score plot 106, they can understand exactly what factors are contributing. To this end, as illustrated in FIG. 9, system 10 provides for a component expansion window 114, such that if the patient has a Health Score of 65 (for example), the expansion might show that the patient lost 12 points due to elevated temperature (over 101 Fahrenheit), lost 18 points due to rapid pulse (between 100 and 110 beats per minute) and lost 5 points due to a pain score of 5; all out of the perfect Health Score of 100.

Figure 10:
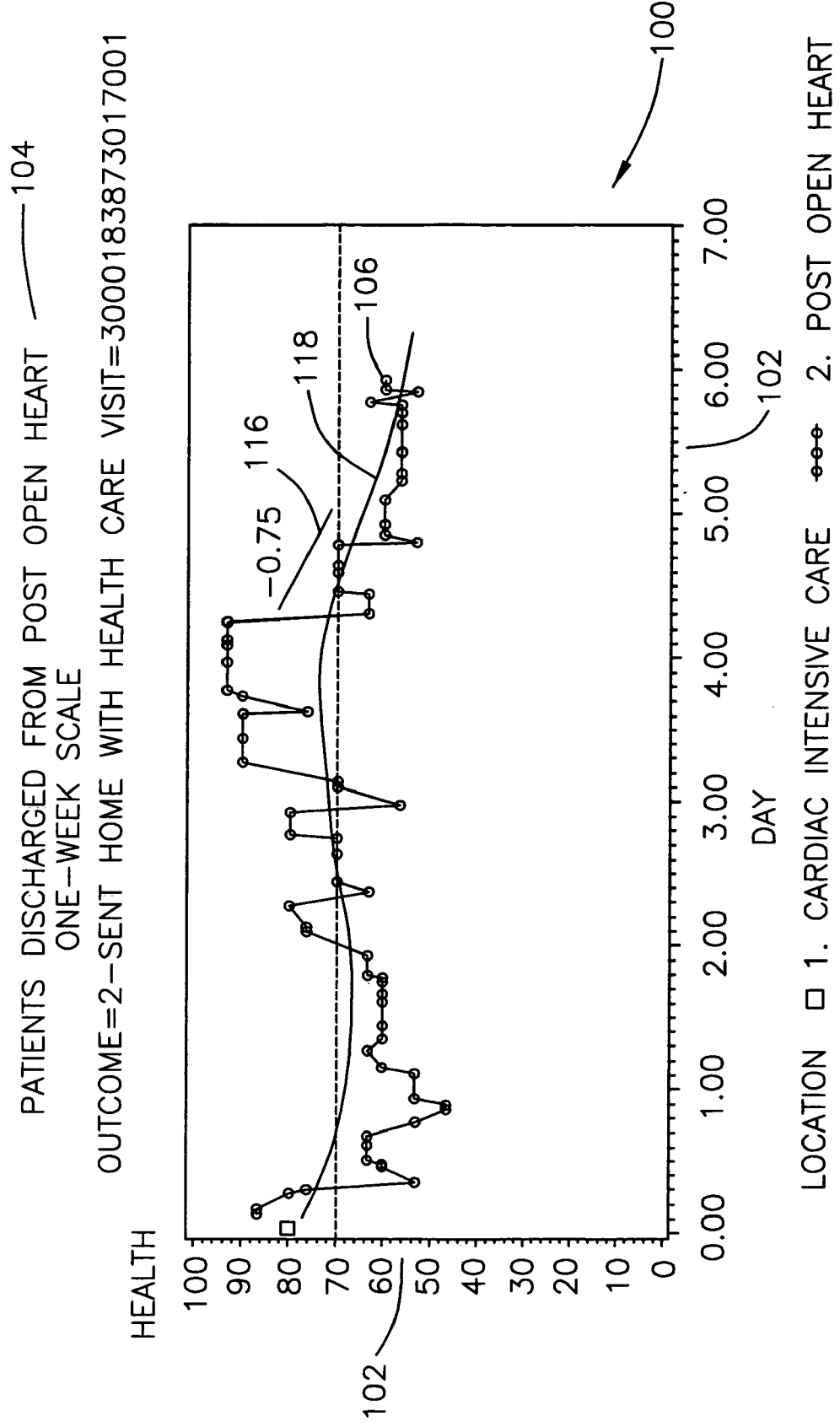
FIG. 10 is a sample Health Score chart as shown in FIG. 4 with additional slope lines, in accordance with one embodiment of the present invention.

In another embodiment, presentation and comparison module 20 may also alter Health Score chart 100 to obtain certain kinds of slope information. Even though trends are usually easy to spot by eye upon looking at Health Score plot 106, an automatic "simple" slope calculation may also be useful. Mathematically, this is the first derivative of the Health Score as a function of time. Due to the "noisiness" of typical Health Score plots 106, some averaging methods may be employed as well. If the slope is positive, the patient is probably getting better; if it is approximately zero, then the patient is staying the same; and if it is negative, then the patient is probably getting worse. Slope lines 116 may be added to the Health Score plot 106, as shown in FIG. 10. Such slope information may help identify trends in Health Score plot 106, particularly, when plot 106 is "noisy" due to large variations between each Health Score measurement. Although normally "staying the same" would not be considered a negative, in the situation where the patient is expected to be recuperating, "staying the same" may be quite worrisome. In the present example, although the most recent Health Scores on plot 106 are constant at about a level of 70, the slope line 116 shows a negative slope, taking into account prior points, including a time early on day 4 when the score was closer to 90.

Presentation and comparison module 20 of system 10 may also compute "rate of change" of the simple slope. For instance, although the patient is still getting better, the rate of improvement may be decreasing. This slow-down in recovery could be evidence of a problem just beginning to develop. Mathematically, this curvature information is the second derivative of Health Score as a function of time. Similar to the slope data 116, due to the "noisiness" of the curves, averaging is included in the computation. It is understood that attending physicians can adjust the slope calculation to include more or less reference Health Scores from plot 100 depending on the time span over which the physician intends to analyze.

When the raw data is noisy, a "running average" or other "smoothing" of the Health Score can be displayed on Health Score charts. The smoothed Health Score curve 118, shown in FIG. 10, could incorporate both the $1^{st}$ derivative (slope) and/or the $2^{nd}$ derivative (curvature) by color-coding or by thickness of the displayed line. For example, if the patient was getting worse (negative slope), the line might be colored red. If the patient is getting worse at an accelerating rate, or is getting better at a lessening rate, then the line could be bolded for emphasis.

Figure 11:
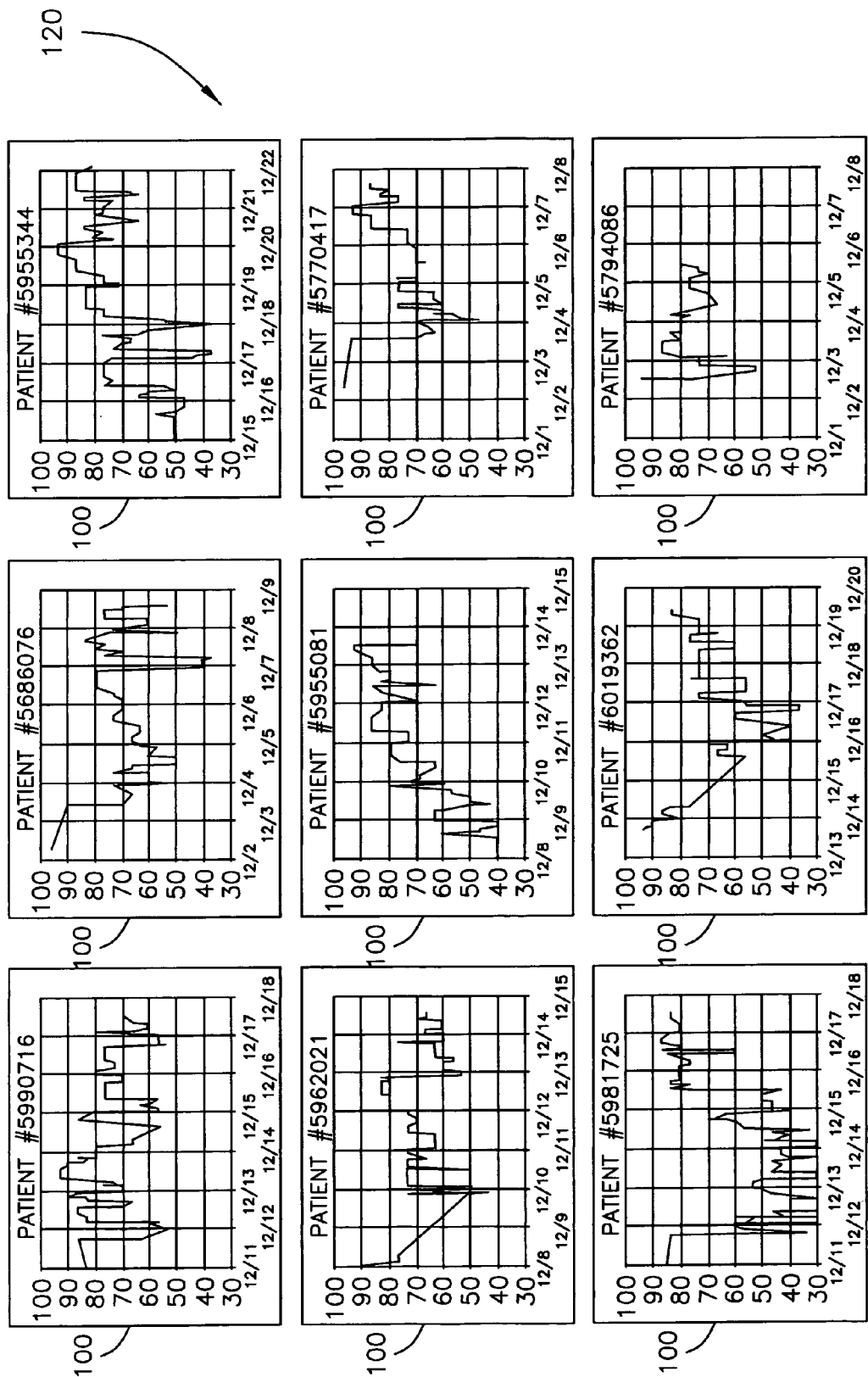
FIG. 11 is a panel of Health Score charts as shown in FIG. 4, in accordance with one embodiment of the present invention.

Presentation and comparison module 20 may further display a panel of Health Score charts 120, as shown in FIG. 11. Typically, a nurse or a doctor or a unit supervisor wants to see, on a single page, the graphs for all the patients in their care. Therefore, system 10 provides for the creation of a patient panel 120, displaying a series of Health Score charts 100. Patient IDs can be included in the label data 104 to identify each chart 100 on panel 120. This is especially useful because an attending physician may wish to appoint more of his time to patients with falling Health Scores (rather than rising ones), given that those patients with falling scores will likely require more attention and given that the physician's time is usually very limited.

It is understood that such modifications to patient Health Score charts 100 are intended only as example modification and are in no way intended to limit the scope of the present invention. Any similar invention that utilizes modified Health Score charts 100 is also within the contemplation of the present invention.

In one embodiment of the present invention, as illustrated in FIG. 1, alert module 22 may send an alert to an attending physician or supervising nurse that a Health Score of a particular patient has fallen below a pre-determined threshold at step 220. For example, if an attending physician sets a threshold of 70, then patients falling below such a level will cause alert module 22 to send an alert message to system terminal 10B at nursing station 32. Although the physician may wish to see Health Score charts 100, regardless of the alerts, alert module 22 acts a reserve precaution warning of the general failing health conditions of a patient who may be approaching a crisis situation. It is understood that the alert may actually be set to an upper threshold as well. Keeping physicians aware of improving health conditions of certain patients may be useful in making discharge decisions or in adjusting medication. Alerts may also be triggered by a fall of so many points in Health Score or by a slope that is of a sufficient negative magnitude.

As such, the above-described system 10 and accompanying generated Health Score charts 100 provide a convenient means for monitoring patient health status, particularly in hospital post-operational situations. It allows doctors to get a feel for the overall health of the patient and to detect trends in the patient's health. Such information is particularly useful in preventing crisis situations from arising in patients, where the worsening condition (of a patient of adequate, yet deteriorating health) is overlooked until it is too late. The creation of the Health Score chart 100, by the present invention, helps in alerting attending physicians, nurses, or "rapid response teams" to deteriorating conditions, even when a spot check of the patient's health would seem to show the patient to be in an adequate state of health.

In addition to the uses outlined above, the Health Score can be used for statistical analysis. For example, the Health Score and the Health Score charts 100 can be used in retrospective research. Many studies of drugs and procedures are published monthly. These studies would benefit from the inclusion of a readily computable Health Score.

For example, a procedure is often evaluated in terms of mortality rate, length of hospital stay, or number of re-admissions to the hospital. These measures are all significant, but at the same time are all rather crude measures. For example, if "Procedure A" has a mortality rate of 0.5% and "Procedure B" has a mortality rate of 0.7%, it may be very difficult to judge one the superior of the other, using only these mortality statistics. However, if patients discharged after Procedure A have an average Health Score of 80, and those discharged after Procedure B have an average Health Score of 60, there may be a real and meaningful difference between the two procedures in terms of overall efficacy in treating the patient. Thus, system 10 may provide a more sensitive measurement of health than any other available measure, since it is not based solely on major "outcomes" (like discharge or death), but rather on a more subtle combination of overall health factors. A medical study using the Health Score, which this invention makes readily available for every patient, would find earlier and easier and more meaningful "statistical significance" than a similar study that needed to wait for eventual mortality outcomes.

Figure 12:
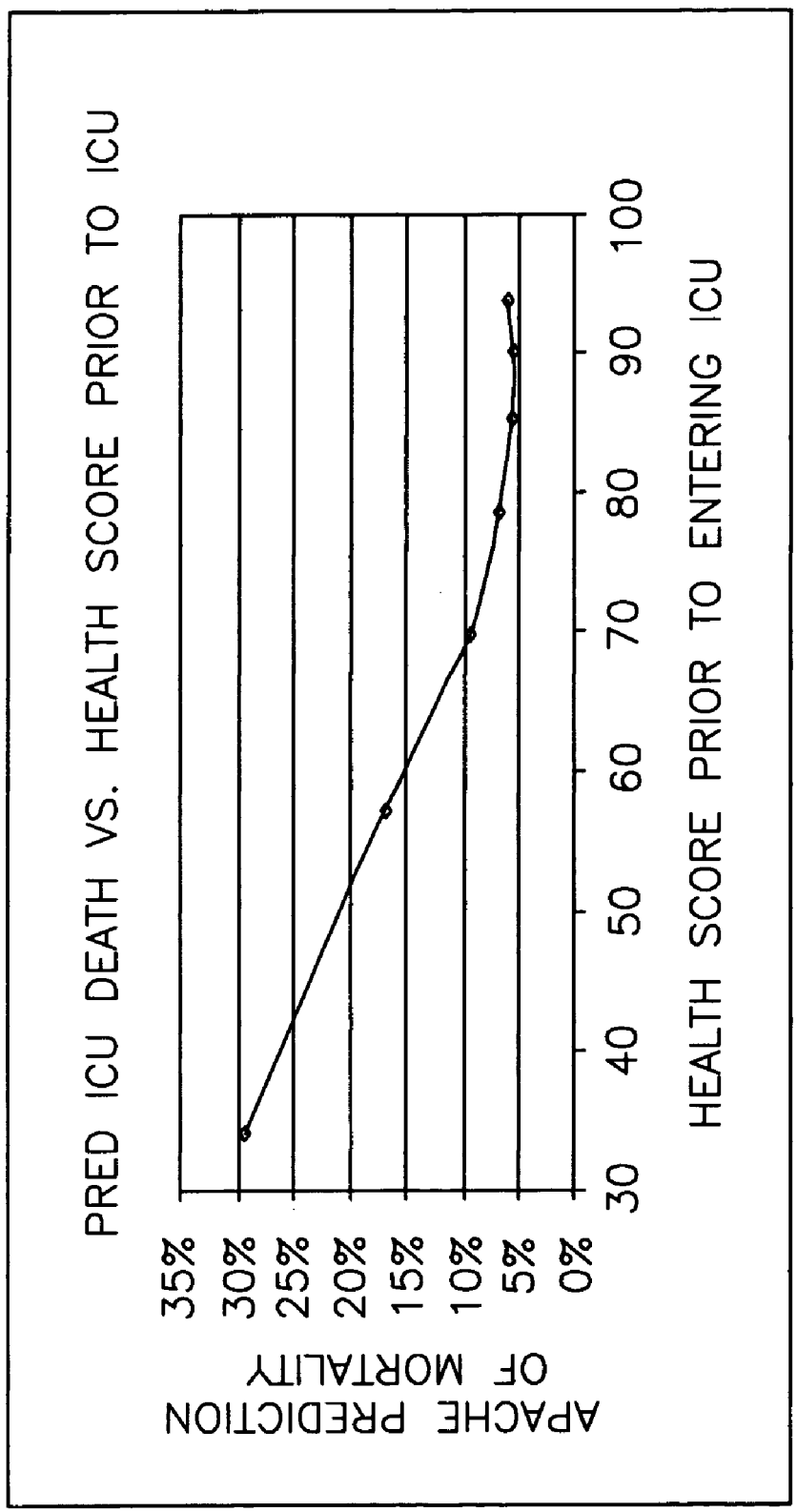
FIG. 12 is a chart showing the correlation between patient Health Scores and rate of expiration, in accordance with one embodiment of the present invention.

An additional feature of Health Scores generated by system 10 is that the Health Score can be used as a predictor to assist in determining which patients require the most care. Although individual symptoms and raw medical data may be varied, the amalgamated Health Score, as shown on Health Score charts 100, tends to be an accurate predictor of patient outcome. For instance, using Health Score data generated post facto, FIG. 12 shows actual graphic correlation between Health Scores from system 10 (computed at transfer to the ICU from a regular ward of the hospital) versus the rate of predicted expiration after an ICU stay. The chart shows a precipitous decline in survival rates when the patient has, incoming to the ICU, an overall Health Score below 65. In such instances, ICU units admitting patients with Health Scores below 65 may choose to divert additional resources to these patients, in order to reduce morbidity and mortality rates. The Health Score is a sensitive new tool for the ICU use. In this example, patient "A" with a Health Score of 65, versus patient "B" with a Health Score of 75, might not exhibit obviously different symptoms, and thus the patients might be treated similarly if the Health Score were not available. But when the doctors know that there is a statistically significant decline in survival rate when the Health Score is 65, patient "A" may get the additional care that would save his life.

Furthermore, incoming Health Scores can be used as an indicator of survival rates before undergoing certain procedure. Not all patients are equal when entering the hospital for a procedure. In some cases, a decision "not to operate" may be made if the risks of complication are too great. An admission-timed Health Score from system 10 may also provide statistical information for post-operative survival rates, which could greatly influence a hospital's decision to recommend the use of surgery, versus alternative treatments.

While only certain features of the invention have been illustrated and described herein, many modifications, substitutions, changes or equivalents will now occur to those skilled in the art. It is therefore, to be understood that this application is intended to cover all such modifications and changes that fall within the true spirit of the invention.

What is claimed is:

1. A system for improving hospital patient care by continually plotting and displaying health scores as a function of time, the system comprising:
    an interface module, executing on a computer, for receiving incoming disparate medical data relating to a patient collected at a point in time, the incoming disparate medical data including at least one datum from a nursing assessment, wherein the nursing assessment is performed by a nurse;
    a transformation module, executing on a computer, for transforming each of the incoming disparate medical data collected at the point in time into a transformed numerical quantity health score value, wherein each of the transformed health score values are in a format for combining together;
    a combination module, executing on a computer, for combining each of the transformed health score values corresponding to each of the incoming disparate medical data into a single health score, the single health score representing the health of the patient at the point in time at which the incoming disparate medical data was collected; and
    a presentation and comparison module, executing on a computer, for continually plotting and displaying on a health score plot single health scores that have been calculated for the patient as a function of time, wherein each of the single health scores displayed at a given point in time are recalculated using any new incoming disparate medical data and represent the health of the patient at the given point in time, such that a user may identify health trends in the patient as a function of time by evaluating the health score plot.

2. The system of claim 1 further comprising:
    a storage module, executing on a computer, for storing past health scores and related historical medical data of the patient; and
    a collection module, executing on a computer, for receiving the incoming disparate medical data from the interface module and for collecting the stored past health scores and related historical medical data of the patient from the storage module, wherein the collection module sends the incoming disparate medical data and the stored past health scores and related historical medical data of the patient to at least one of the transformation module and the presentation and comparison module.

3. The system of claim 1, further comprising an alert module, executing on a computer, for alerting the user when a health score falls below a predetermined threshold.

4. The system of claim 1, wherein the transformation module transforms each of the incoming disparate medical data into a scaled number and wherein the combination module adds together the scaled numbers, and applies a predetermined algorithm to the added scaled numbers to generate the health score.

5. The system of claim 4, wherein the user can modify the algorithm used to generate the single health score based on an illness or condition of the patient.

6. The system of claim 1, wherein the presentation and comparison module includes a statistical reference curve on the health score plot.

7. The system of claim 1, wherein the presentation and comparison module further supplies principal corresponding measurements of direct medical data on the health score plot.

8. The system of claim 1, wherein the presentation and comparison module displays a smoothed health score curve that provides a running average of the health score plot over time.

9. The system of claim 8, wherein the smoothed health score curve plot incorporates at least one of a slope and a curvature.

10. The system of claim 1, wherein the at least one datum from the nursing assessment includes at least one of: respiration, pain, cardiac, gastrointestinal, genitourinary, nutrition, musculoskeletal, skin, Braden score, neurological, psychosocial, peripheral vascular, and safety.

11. A method for improving hospital patient care by continually plotting and displaying health scores as a function of time, the method comprising the steps of:
    receiving, on a computer, incoming disparate medical data related to a patient and collected at a point in time at an interface module, the incoming disparate medical data including at least one datum from a nursing assessment, wherein the nursing assessment is performed by a nurse;
    transforming, on a computer, each of the incoming disparate medical data collected at the point in time into a transformed numerical quantity health score value at a transformation module, wherein each of the transformed health score values are in a format for combining together;

combining, on a computer, each of the transformed health score values corresponding to each of the incoming disparate medical data into a single health score at a combination module, the single health score representing the health of the patient at the point in time at which the incoming disparate medical data was collected;

generating, on a computer, a health score plot of single health scores that have been calculated for the patient as a function of time at a presentation and comparison module, wherein each of the single health scores are recalculated using any new incoming disparate medical data and represent the health of the patient at a point in time; and continually plotting and displaying, on a computer, the health score plot such that a user may identify health trends in the patient as a function of time by evaluating the health score plot.

12. The method of claim 11, further comprising the steps of:

storing, on a computer, past health scores and related historical medical data of the patient in a storage module;

receiving, on a computer, the incoming disparate medical data from the interface module;

collecting, on a computer, the stored past health scores and related historical medical data of the patient from the storage module at a collection module; and sending, on a computer, the incoming disparate medical data and the stored past health scores and related historical medical data of the patient to at least one of the transformation module and the presentation and comparison module.

13. The method of claim 11, further comprising the step of alerting, on a computer, the user when a single health score falls below a predetermined threshold via an alert module.

14. The method of claim 11, further comprising the steps of:

converting, on a computer, each of the incoming disparate medical data into a scaled number at the transformation module;

adding, on a computer, the scaled numbers; and applying, on a computer, a predetermined algorithm to the added scaled numbers to generate a health score at the combination module.

15. The method of claim 14, wherein the algorithm used to generate the single health score is modified based on an illness or condition of the patient.

16. The method of claim 11, further comprising the step of: including a statistical reference curve on the health score plot via the presentation and comparison module so that the health score plot can be compared to a health score plot of a patient with similar conditions and circumstances.

17. The method of claim 11, wherein the presentation and comparison module further supplies principal corresponding measurements of direct medical data on the health score plot.

18. The method of claim 11, wherein the presentation and comparison module displays a smoothed health score curve that provides a running average of the health score plot over time.

19. The method of claim 18, wherein the smoothed health score curve incorporates at least one of a slope and a curvature.

20. The method of claim 11, wherein the at least one datum from the nursing assessment includes at least one of: respiration, pain, cardiac, gastrointestinal, genitourinary, nutrition, musculoskeletal, skin, Braden score, neurological, psychosocial, peripheral vascular, and safety.

* * * * *